(12) United States Patent
Schaller et al.

(10) Patent No.: US 10,966,696 B2
(45) Date of Patent: Apr. 6, 2021

(54) CATHETER-BASED TISSUE REMODELING DEVICES AND METHODS

(71) Applicant: Laurent Schaller, Los Altos, CA (US)

(72) Inventors: Laurent Schaller, Los Altos, CA (US); Joseph Trautman, Sunnyvale, CA (US)

(73) Assignee: Laurent Schaller, Los Altos, CA (US)

( * ) Notice: Subject to any disclaimer, the term of this patent is extended or adjusted under 35 U.S.C. 154(b) by 0 days.

(21) Appl. No.: 17/095,032

(22) Filed: Nov. 11, 2020

(65) Prior Publication Data
US 2021/0059652 A1 Mar. 4, 2021

Related U.S. Application Data

(60) Continuation of application No. 14/827,707, filed on Aug. 17, 2015, which is a division of application No.
(Continued)

(51) Int. Cl.
A61F 2/24 (2006.01)
A61B 17/00 (2006.01)
(Continued)

(52) U.S. Cl.
CPC .... *A61B 17/00234* (2013.01); *A61B 17/0401* (2013.01); *A61B 17/0469* (2013.01); *A61B 17/0482* (2013.01); *A61F 2/2478* (2013.01); *A61B 17/0487* (2013.01); *A61B 17/064* (2013.01); *A61B 17/068* (2013.01); *A61B 2017/00243* (2013.01); *A61B 2017/00318* (2013.01); *A61B 2017/00575* (2013.01); *A61B 2017/0409* (2013.01);
(Continued)

(58) Field of Classification Search
None
See application file for complete search history.

(56) References Cited

U.S. PATENT DOCUMENTS 4,235,238 A 11/1980 Ogiu et al.
4,841,888 A 6/1989 Mills et al.
(Continued)

FOREIGN PATENT DOCUMENTS

WO WO 00/07521 2/2000
WO WO 01/01868 A1 1/2001
WO WO-2005046488 A2 * 5/2005 ....... A61B 17/00234

*Primary Examiner* — Shaun L David
(74) *Attorney, Agent, or Firm* — Cook Alex Ltd.

(57) ABSTRACT

Methods and systems for closing an opening or defect in tissue, closing a lumen or tubular structure, cinching or remodeling a cavity or repairing a valve preferably utilizing a purse string or elastic device. The preferred devices and methods are directed toward catheter-based percutaneous, transvascular techniques used to facilitate placement of the devices within lumens, such as blood vessels, or on or within the heart to perform structural defect repair, such as valvular or ventricular remodeling. In some methods, the catheter is positioned within the right ventricle, wherein the myocardial wall or left ventricle may be accessed through the septal wall to position a device configured to permit reshaping of the ventricle. The device may include a line or a plurality of anchors interconnected by a line. In one arrangement, the line is a coiled member.

16 Claims, 26 Drawing Sheets

Related U.S. Application Data

13/712,651, filed on Dec. 12, 2012, now Pat. No. 9,107,658, which is a division of application No. 11/408,717, filed on Apr. 21, 2006, now Pat. No. 8,333,777.

(60) Provisional application No. 60/702,823, filed on Jul. 27, 2005, provisional application No. 60/673,838, filed on Apr. 22, 2005.

(51) Int. Cl.
  *A61B 17/04*    (2006.01)
  *A61B 17/064*    (2006.01)
  *A61B 17/068*    (2006.01)
  *A61B 17/06*    (2006.01)

(52) U.S. Cl.
  CPC ............... *A61B 2017/0414* (2013.01); *A61B 2017/0417* (2013.01); *A61B 2017/0458* (2013.01); *A61B 2017/0461* (2013.01); *A61B 2017/0464* (2013.01); *A61B 2017/0472* (2013.01); *A61B 2017/0496* (2013.01); *A61B 2017/06052* (2013.01); *A61F 2/2442* (2013.01); *A61F 2/2466* (2013.01); *A61F 2/2487* (2013.01); *A61F 2002/249* (2013.01)

(56) References Cited

U.S. PATENT DOCUMENTS

| | | |
|---|---|---|
| 4,925,443 A | 5/1990 | Hellman et al. |
| 5,002,563 A | 3/1991 | Pyka et al. |
| 5,030,228 A | 7/1991 | Wong |
| 5,156,609 A | 10/1992 | Nakao et al. |
| 5,549,631 A | 8/1996 | Bonutti |
| 5,591,180 A | 1/1997 | Hinchliffe |
| 5,607,435 A | 3/1997 | Sachdeva et al. |
| 5,695,504 A | 12/1997 | Gifford et al. |
| 5,792,153 A | 8/1998 | Swain et al. |
| 5,797,933 A | 8/1998 | Snow et al. |
| 5,865,791 A | 2/1999 | Whayne et al. |
| 5,961,440 A | 10/1999 | Schweich, Jr. et al. |
| 6,045,497 A | 4/2000 | Schweich et al. |
| 6,050,936 A | 4/2000 | Schweich, Jr. et al. |
| 6,059,715 A | 5/2000 | Schweich, Jr. et al. |
| 6,071,292 A | 6/2000 | Makower et al. |
| 6,077,214 A | 6/2000 | Mortier et al. |
| 6,079,414 A | 6/2000 | Roth |
| 6,117,144 A | 9/2000 | Nobles et al. |
| 6,143,015 A | 11/2000 | Nobles |
| 6,152,144 A | 11/2000 | Lesh et al. |
| 6,155,968 A | 12/2000 | Wilk |
| 6,165,183 A | 12/2000 | Kuehn et al. |
| 6,193,733 B1 | 2/2001 | Adams |
| 6,231,561 B1 | 5/2001 | Frazier et al. |
| 6,290,674 B1 | 9/2001 | Roue et al. |
| 6,306,163 B1 | 10/2001 | Fitz |
| 6,332,893 B1 | 12/2001 | Mortier et al. |
| 6,346,074 B1 | 2/2002 | Roth |
| 6,360,749 B1 | 3/2002 | Jayaraman |
| 6,406,420 B1 | 6/2002 | McCarthy et al. |
| 6,461,366 B1 | 10/2002 | Seguin |
| 6,561,969 B2 | 5/2003 | Frazier et al. |
| 6,619,291 B2 | 9/2003 | Hlavka |
| 6,629,534 B1 | 10/2003 | St. Goar et al. |
| 6,719,767 B1 | 4/2004 | Kimblad |
| 6,726,923 B2 | 4/2004 | Iyer et al. |
| 6,764,510 B2 | 7/2004 | Vidlund |
| 6,776,784 B2 | 8/2004 | Ginn |
| 6,800,081 B2 | 10/2004 | Parodi |
| 6,802,858 B2 | 10/2004 | Gambale et al. |
| 6,808,483 B1 | 10/2004 | Ortiz et al. |
| 6,852,076 B2 | 2/2005 | Nikolic et al. |
| 7,004,176 B2 | 2/2006 | Lau |
| 7,063,710 B2 | 6/2006 | Takamoto et al. |
| 7,087,064 B1 | 8/2006 | Hyde |
| 7,101,395 B2 | 9/2006 | Tremulis |
| 7,175,636 B2 | 2/2007 | Yamamoto et al. |
| 7,431,726 B2 | 10/2008 | Spence et al. |
| 7,833,238 B2 | 11/2010 | Nakao |
| 8,287,555 B2 | 10/2012 | Starksen et al. |
| 8,864,823 B2 | 10/2014 | Cartledge et al. |
| 8,979,923 B2 | 3/2015 | Spence et al. |
| 2002/0029080 A1 | 3/2002 | Mortier et al. |
| 2002/0049453 A1 | 4/2002 | Nobles et al. |
| 2002/0065451 A1 | 5/2002 | Spence |
| 2002/0077524 A1 | 6/2002 | Schweich, Jr. et al. |
| 2002/0120200 A1 | 8/2002 | Brockway et al. |
| 2002/0169359 A1 | 11/2002 | McCarthy et al. |
| 2002/0173694 A1 | 11/2002 | Mortier et al. |
| 2002/0188170 A1 | 12/2002 | Santamore et al. |
| 2002/0193830 A1 | 12/2002 | Bonutti |
| 2003/0032979 A1 | 2/2003 | Mortier et al. |
| 2003/0050685 A1 | 3/2003 | Nikolic et al. |
| 2003/0069592 A1 | 4/2003 | Adams et al. |
| 2003/0078465 A1 | 4/2003 | Pai |
| 2003/0158570 A1 | 8/2003 | Ferrazzi |
| 2003/0171776 A1 | 9/2003 | Adams et al. |
| 2003/0181928 A1 | 9/2003 | Vidlund et al. |
| 2004/0030382 A1 | 2/2004 | St Goar et al. |
| 2004/0039442 A1 | 2/2004 | St. Goar et al. |
| 2004/0097865 A1 | 5/2004 | Anderson et al. |
| 2004/0098047 A1 | 5/2004 | Frazier et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0127913 A1 | 7/2004 | Voss |
| 2004/0127916 A1 | 7/2004 | Bolduc et al. |
| 2004/0127917 A1 | 7/2004 | Ginn |
| 2004/0127983 A1 | 7/2004 | Mortier et al. |
| 2004/0133063 A1 | 7/2004 | McCarthy et al. |
| 2004/0138704 A1 | 7/2004 | Gambale et al. |
| 2004/0138744 A1 | 7/2004 | Lashinski |
| 2004/0147958 A1 | 7/2004 | Lam et al. |
| 2004/0152947 A1 | 8/2004 | Schroeder et al. |
| 2004/0162568 A1 | 8/2004 | Saadat et al. |
| 2004/0162610 A1 | 8/2004 | Liska et al. |
| 2004/0167546 A1 | 8/2004 | Saadat et al. |
| 2004/0172046 A1 | 9/2004 | Hlavka et al. |
| 2004/0186566 A1 | 9/2004 | Hindrichs et al. |
| 2004/0193191 A1 | 9/2004 | Starksen et al. |
| 2004/0199183 A1 | 10/2004 | Oz et al. |
| 2004/0225304 A1 | 11/2004 | Vidlund et al. |
| 2004/0236419 A1 | 11/2004 | Milo |
| 2004/0243227 A1 | 12/2004 | Starksen et al. |
| 2004/0249395 A1 | 12/2004 | Mikkaichi et al. |
| 2005/0043792 A1* | 2/2005 | Solem ............... A61B 17/00234 623/2.36 |
| 2005/0049692 A1 | 3/2005 | Numamoto et al. |
| 2005/0075713 A1 | 4/2005 | Biancucci et al. |
| 2005/0075723 A1 | 4/2005 | Schroeder et al. |
| 2005/0125011 A1 | 6/2005 | Spence |
| 2005/0137700 A1 | 6/2005 | Spence et al. |
| 2005/0177180 A1 | 8/2005 | Kaganov et al. |
| 2005/0187565 A1 | 8/2005 | Baker et al. |
| 2005/0222678 A1 | 10/2005 | Lashinski |
| 2005/0234512 A1 | 10/2005 | Nakao |
| 2005/0245945 A1 | 11/2005 | Ewers et al. |
| 2005/0288694 A1 | 12/2005 | Solomon |
| 2006/0015002 A1 | 1/2006 | Moaddeb et al. |
| 2006/0106456 A9 | 5/2006 | Machold et al. |
| 2006/0229708 A1 | 10/2006 | Powell |
| 2006/0241748 A1 | 10/2006 | Lee |
| 2006/0282161 A1 | 12/2006 | Huynh |
| 2007/0016287 A1 | 1/2007 | Cartledge et al. |
| 2007/0038293 A1 | 2/2007 | St.Goar |
| 2007/0051377 A1* | 3/2007 | Douk ................. A61F 2/2445 128/897 |
| 2007/0080188 A1 | 4/2007 | Spence |
| 2008/0288060 A1 | 11/2008 | Kaye et al. |
| 2020/0155312 A1 | 5/2020 | Gross |

\* cited by examiner

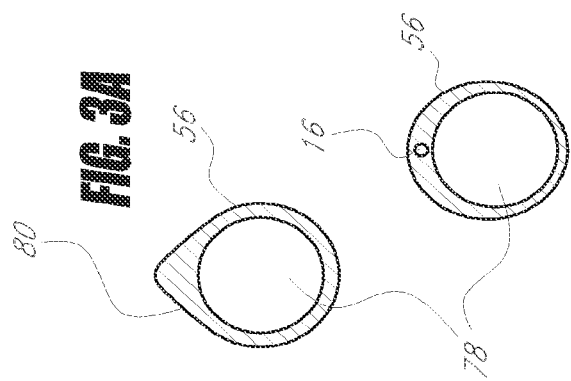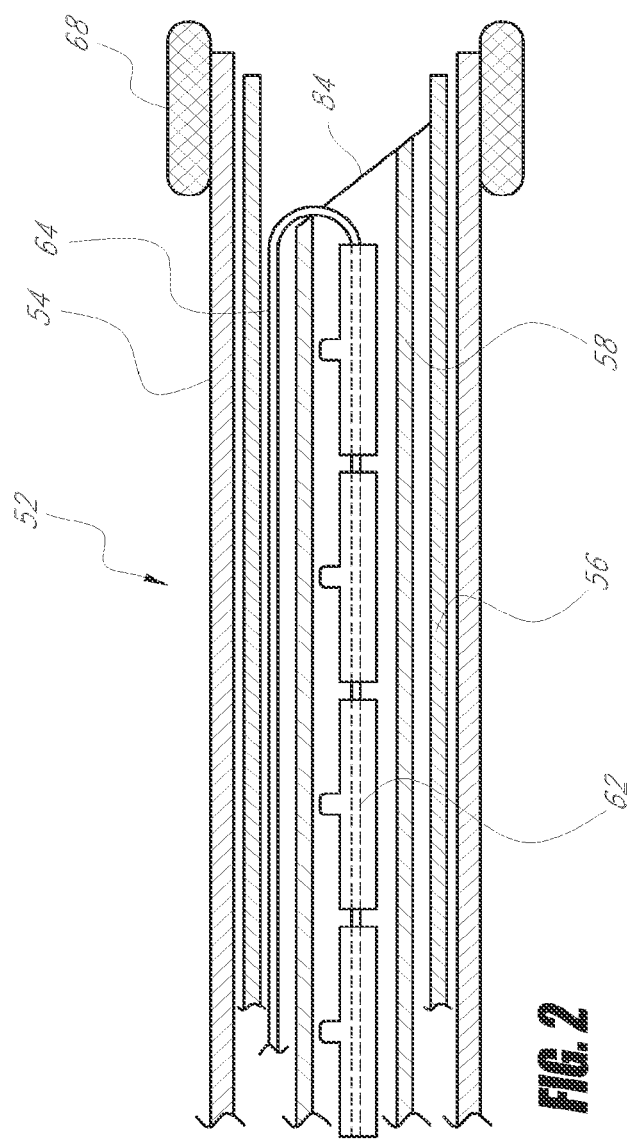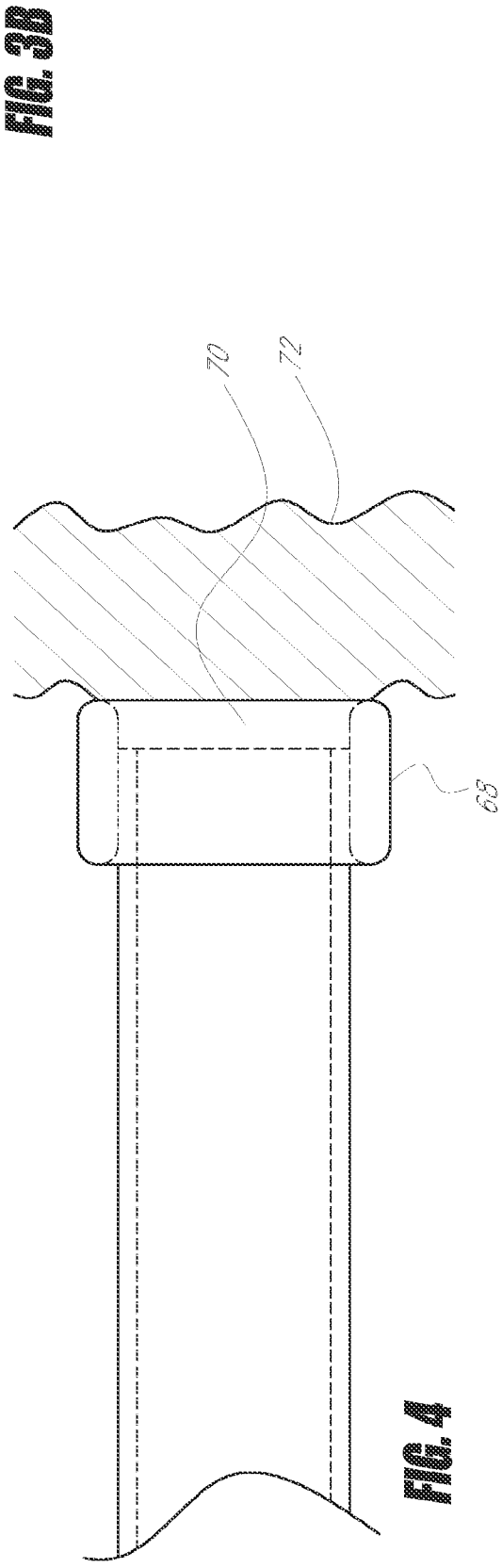

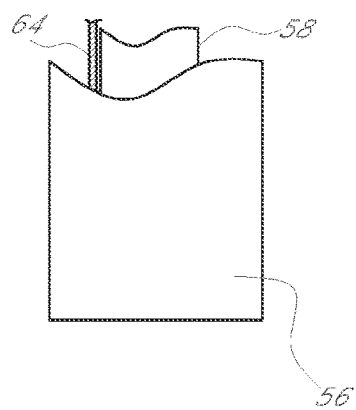
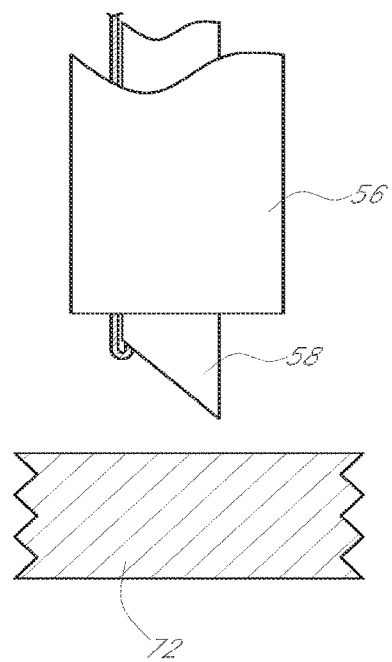
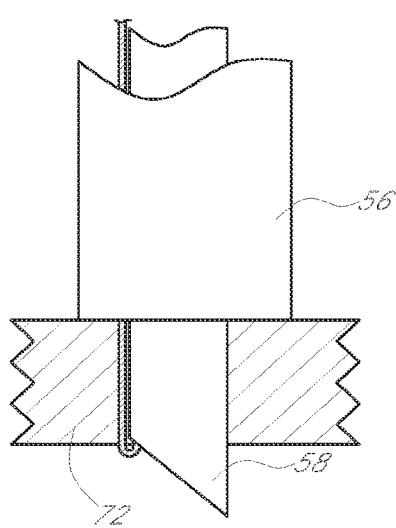
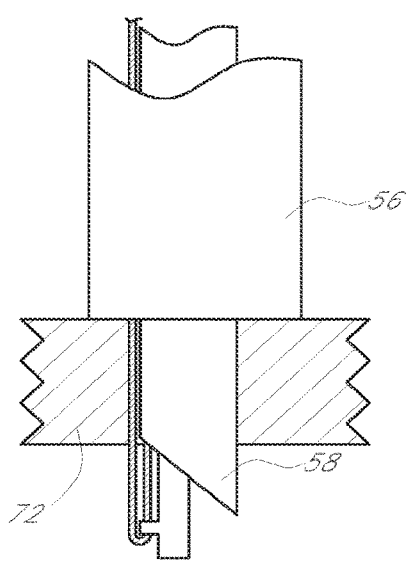
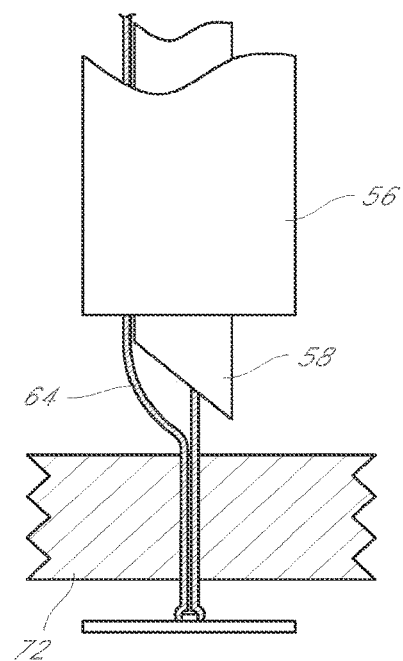

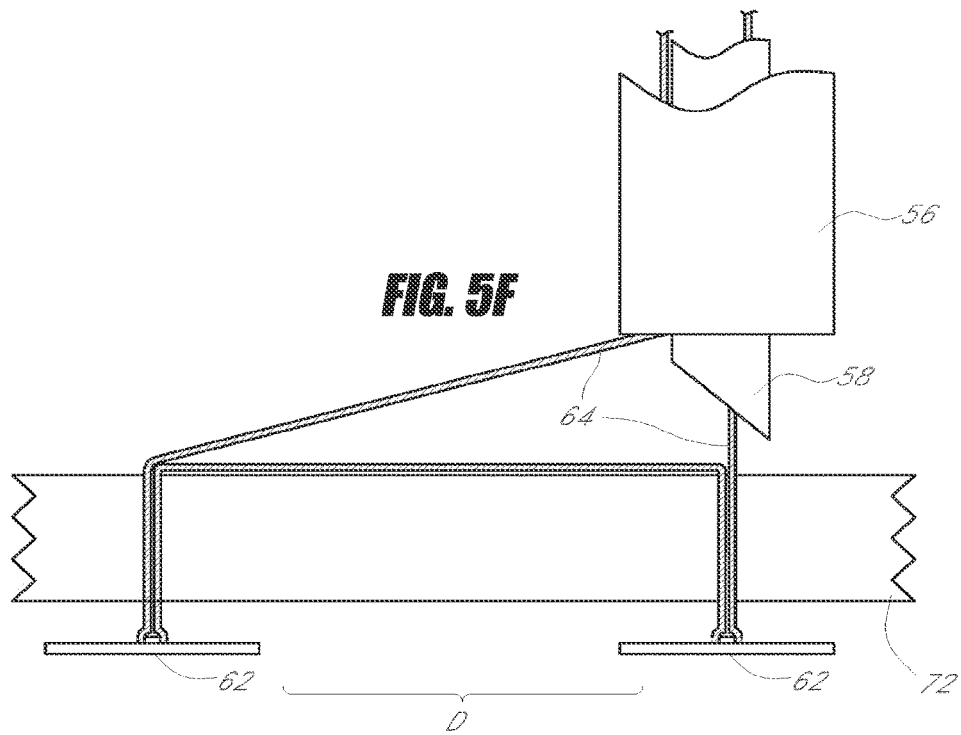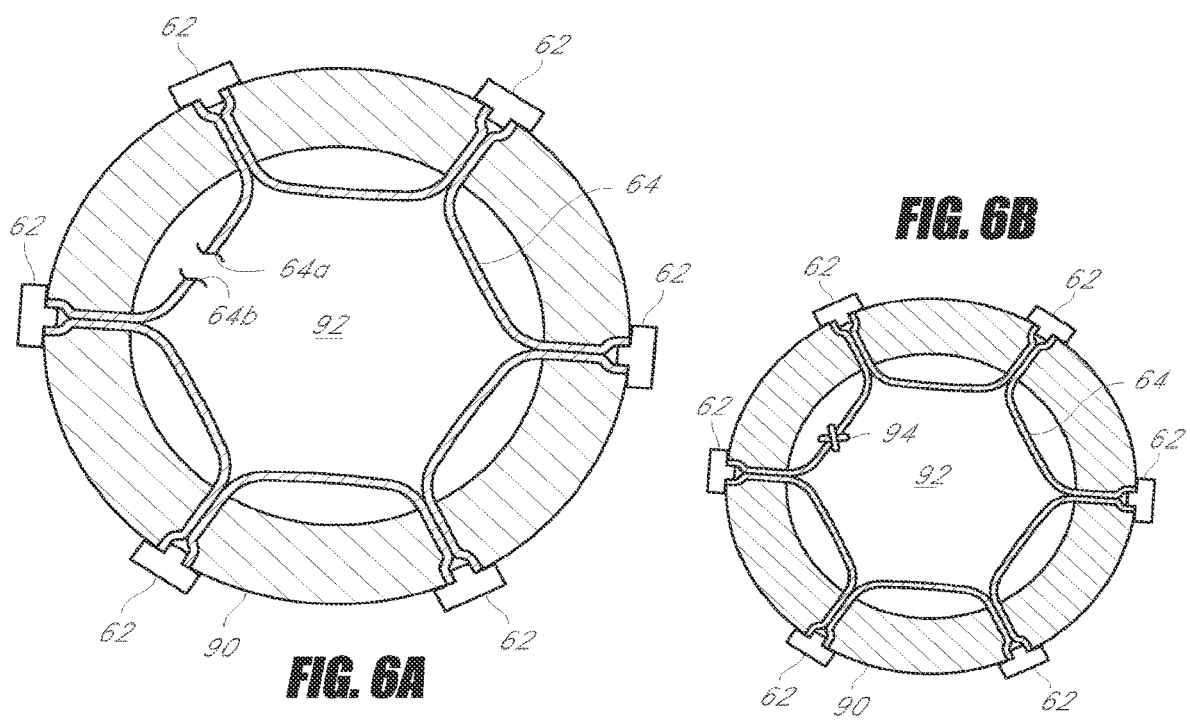

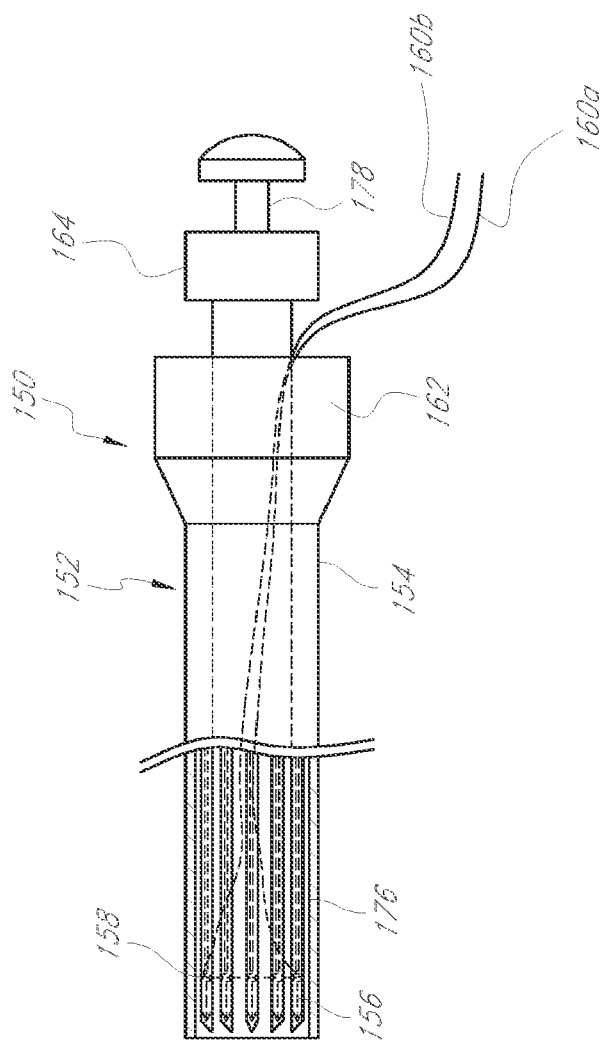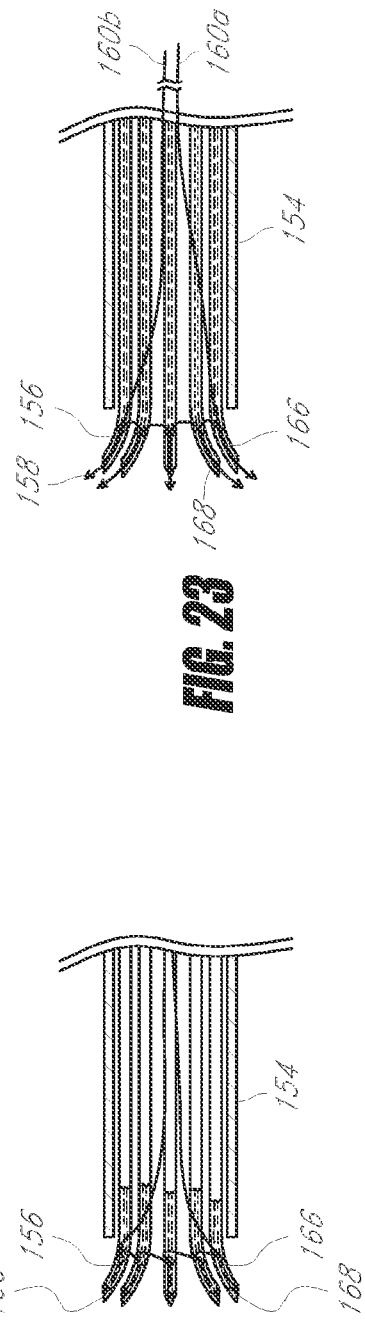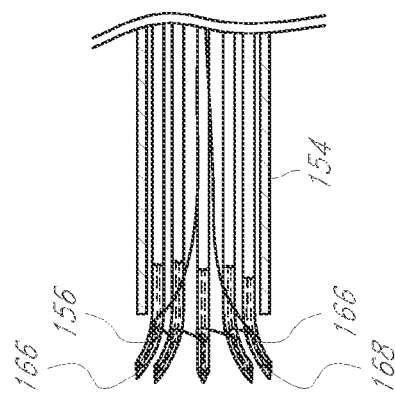

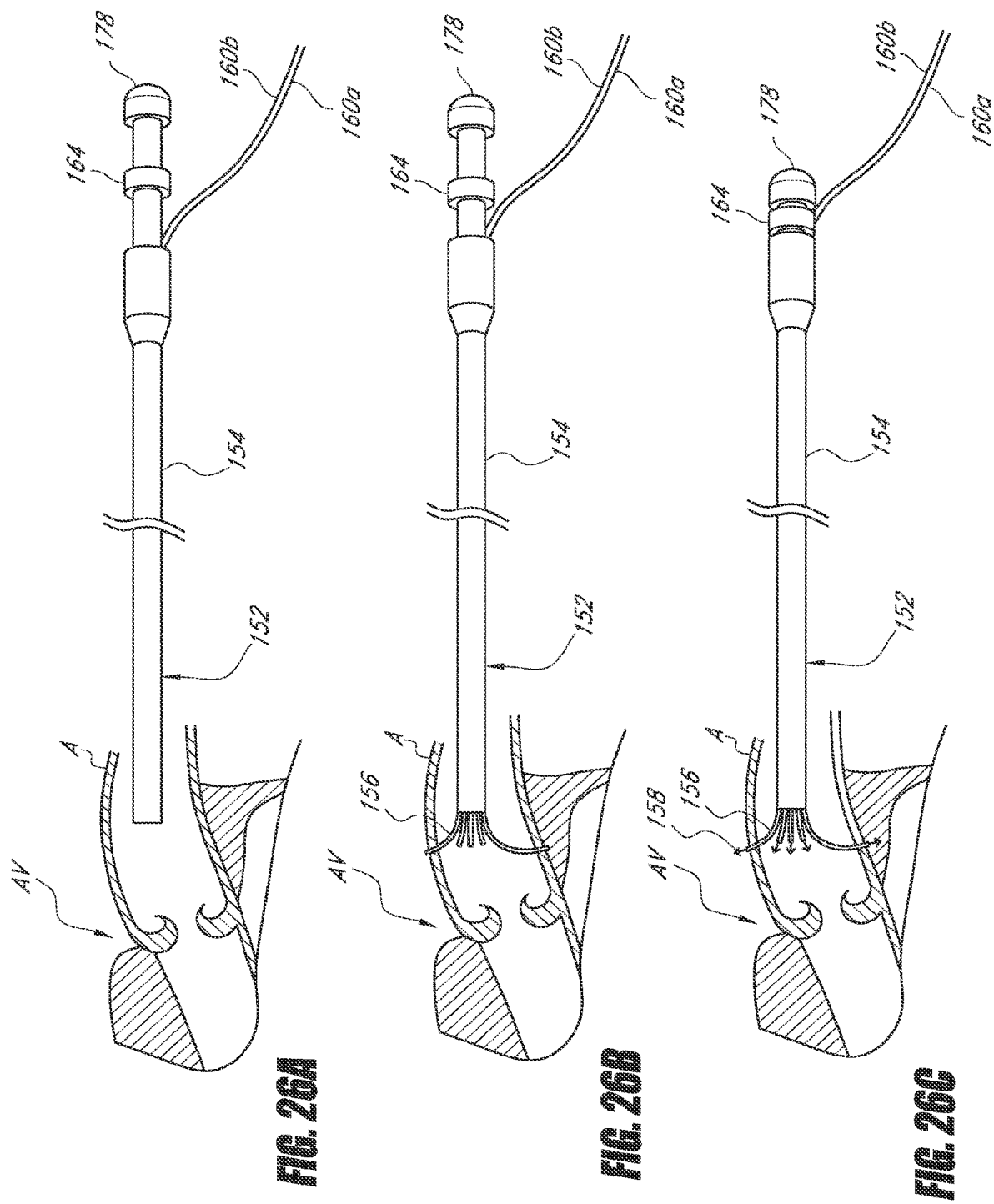

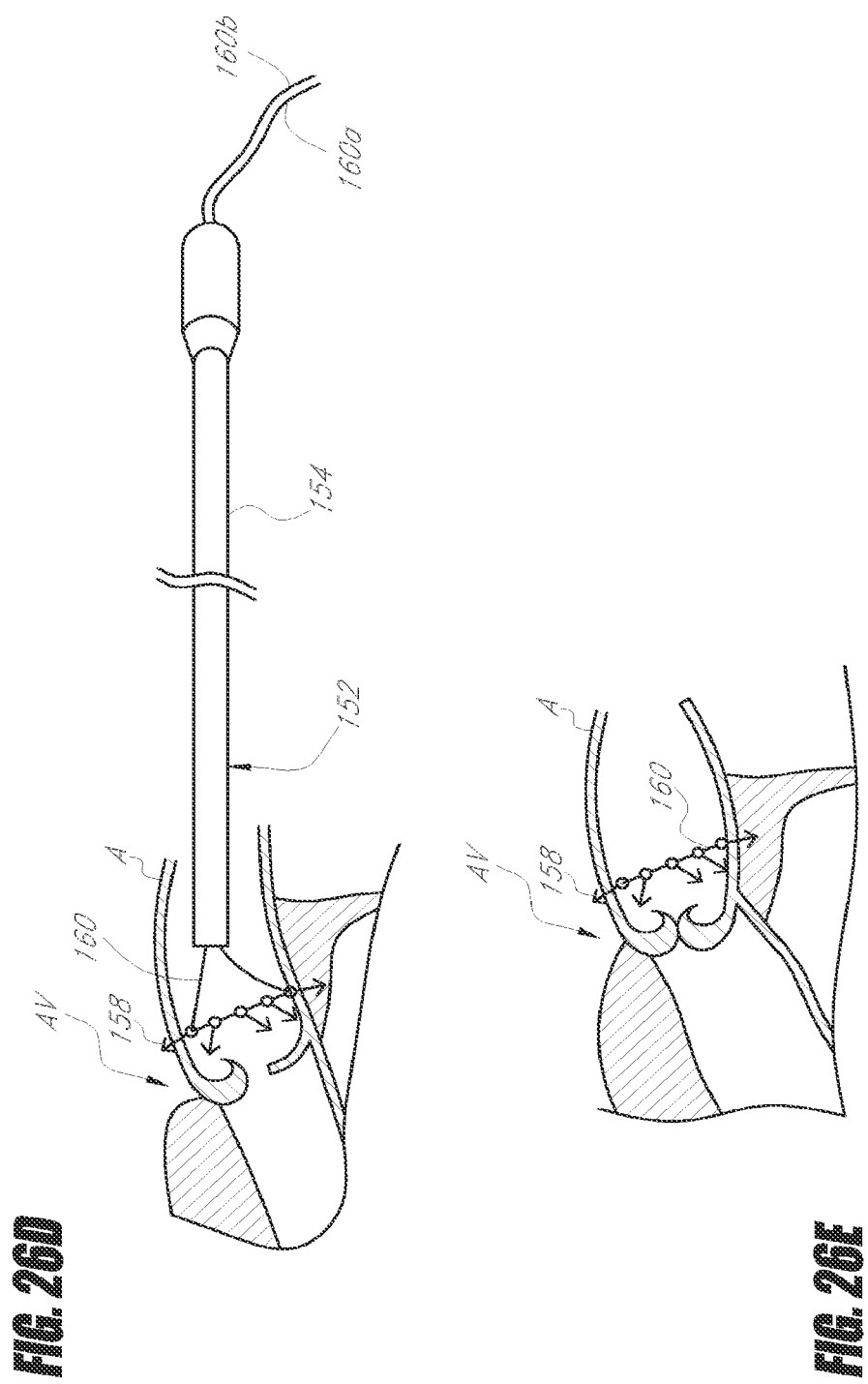

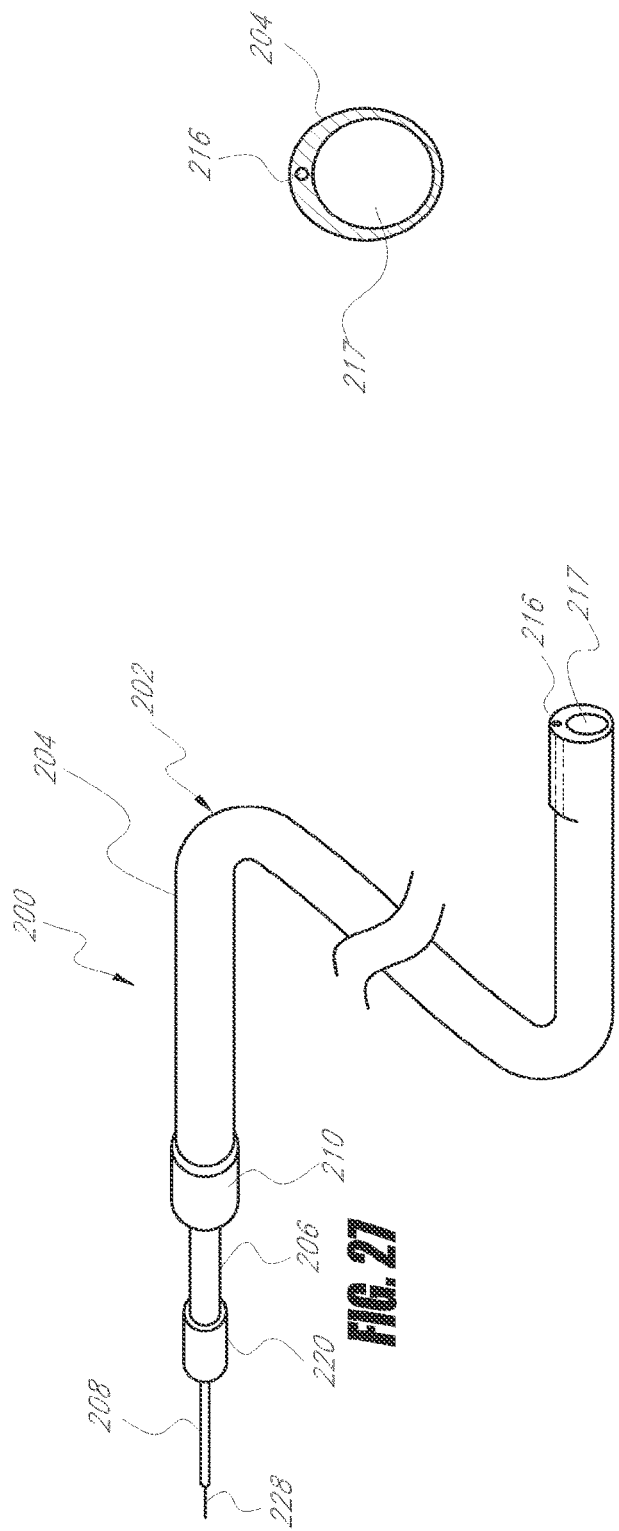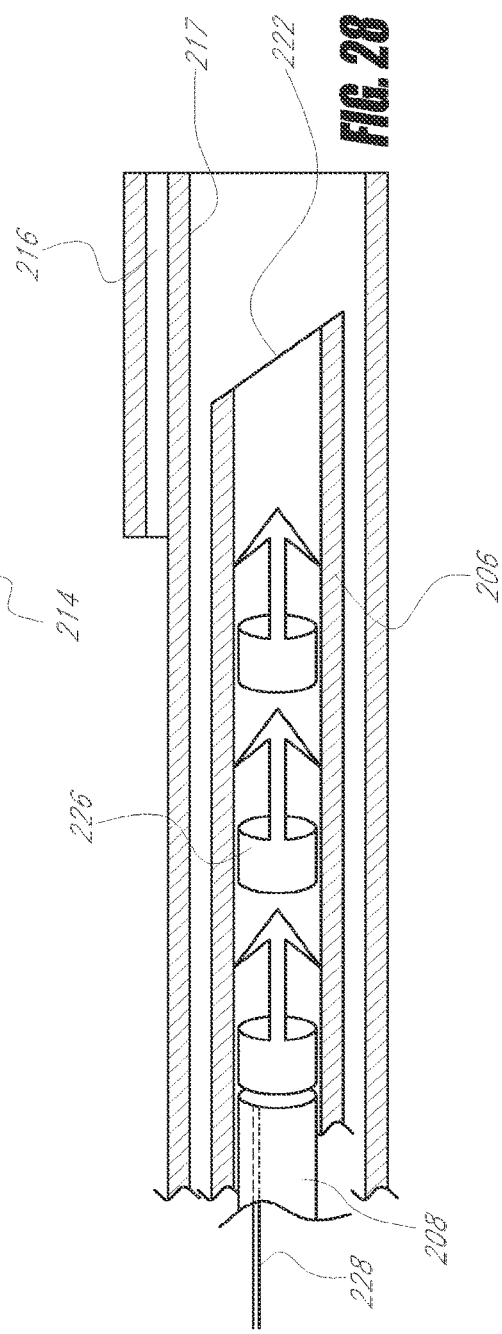

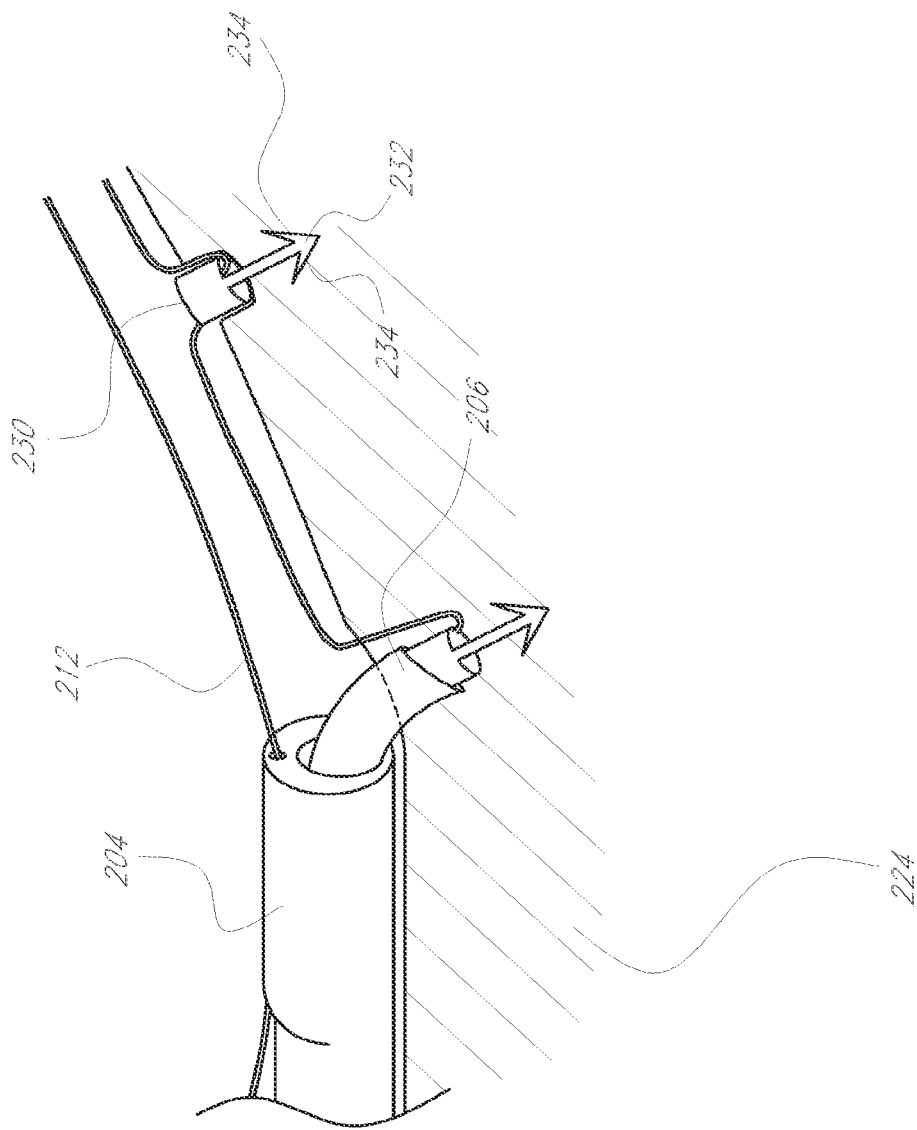

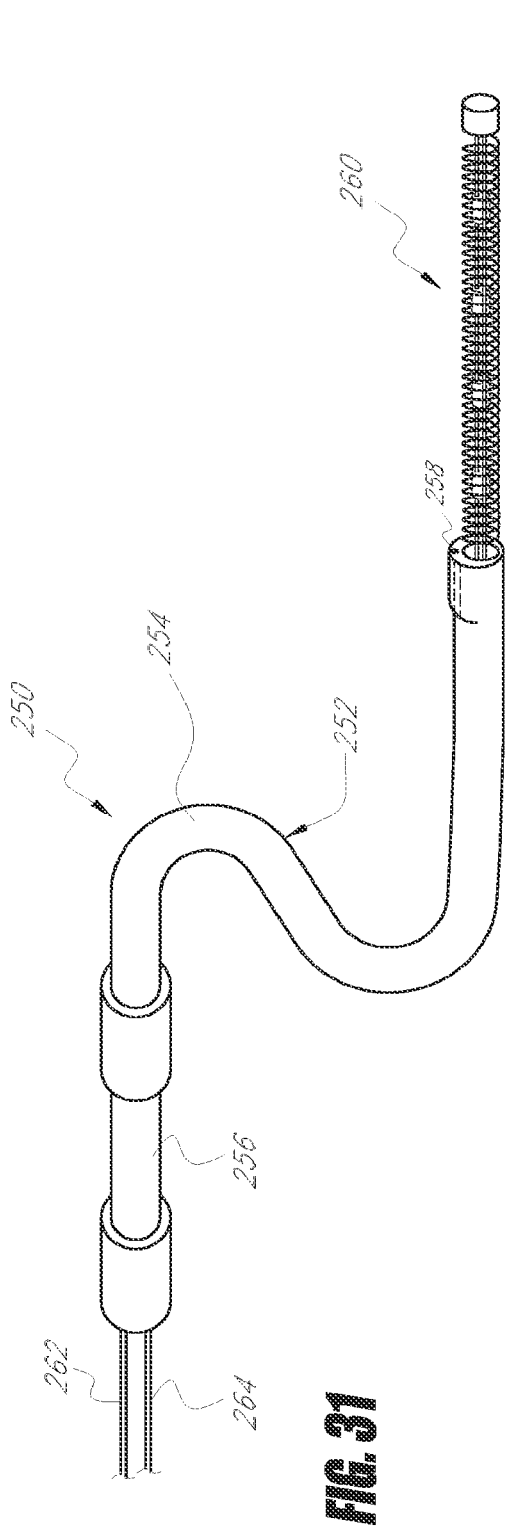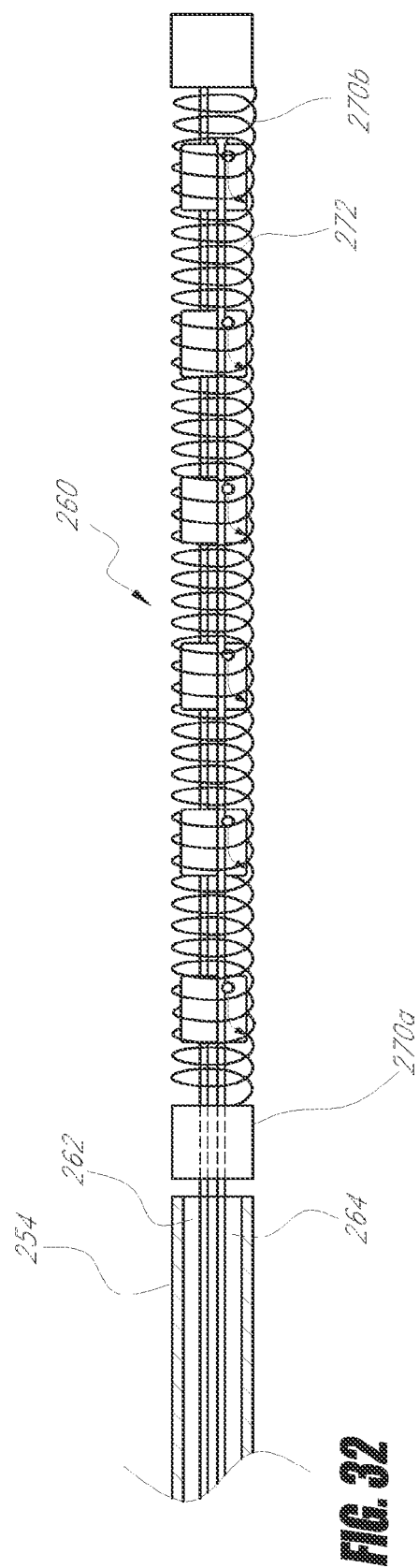

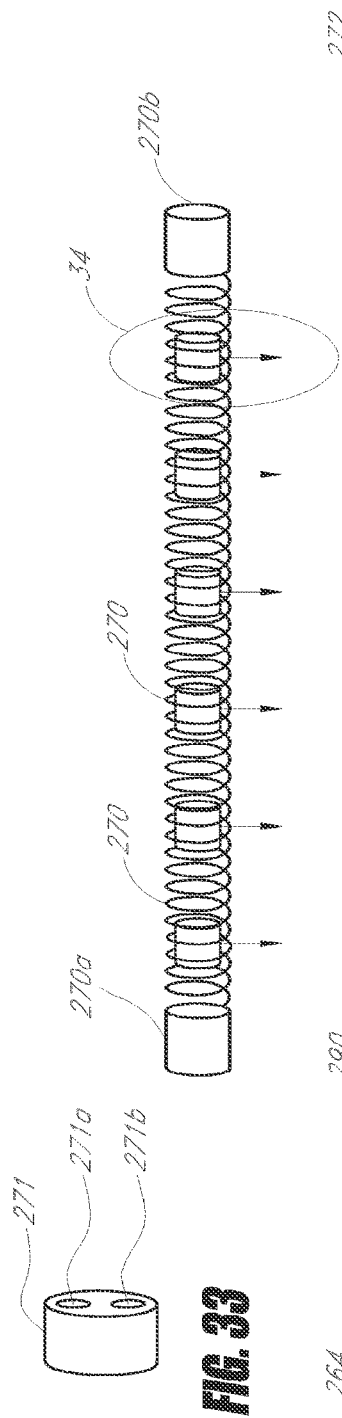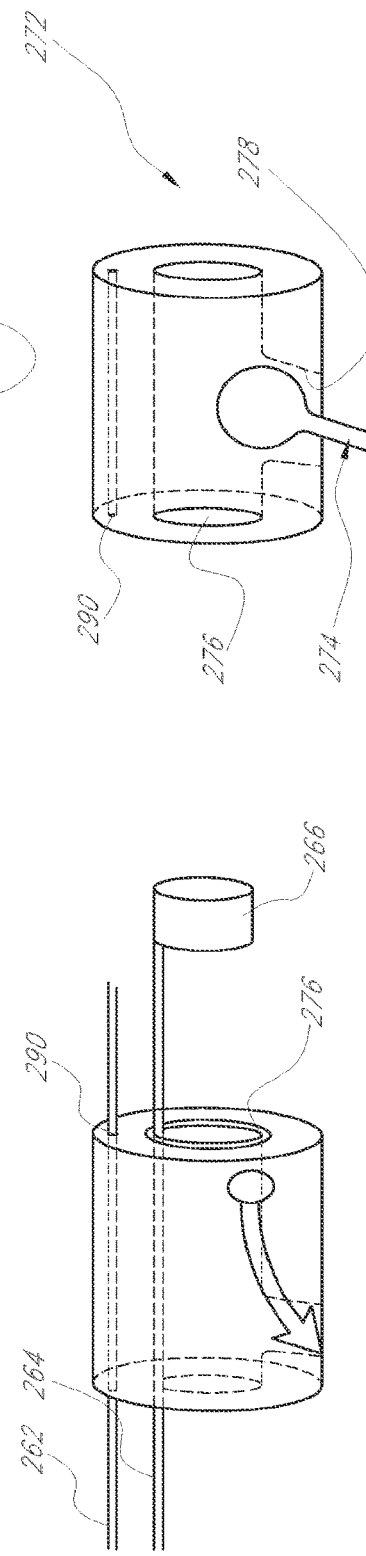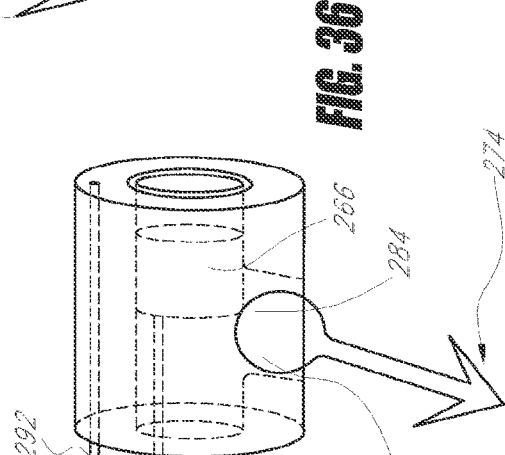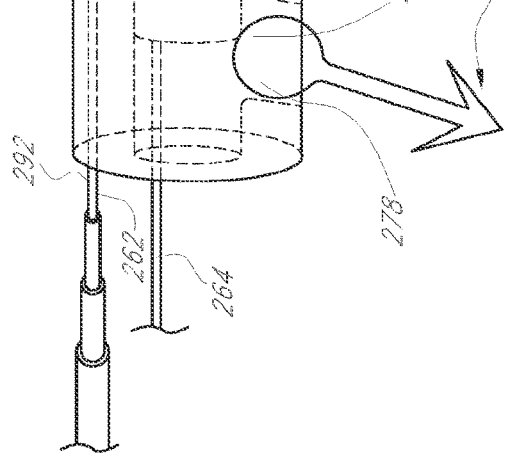

CATHETER-BASED TISSUE REMODELING DEVICES AND METHODS

RELATED APPLICATIONS

This application is a continuation of U.S. patent application Ser. No. 14/827,707, filed Aug. 17, 2015, which is a divisional of U.S. patent application Ser. No. 13/712,651, filed Dec. 12, 2012 (now U.S. Pat. No. 9,107,658, issued Aug. 18, 2015), which is a divisional of U.S. patent application Ser. No. 11/408,717, filed Apr. 21, 2006 (now U.S. Pat. No. 8,333,777, issued Dec. 18, 2012), which is related to, and claims the benefit of priority from, U.S. Provisional Patent Application No. 60/702,823, filed Jul. 27, 2005, and U.S. Provisional Patent Application No. 60/673,838, filed Apr. 22, 2005. The entireties of each of the above referenced applications are hereby incorporated by reference herein and made a part of the present disclosure.

BACKGROUND OF THE INVENTION

Field of the Invention

The present invention relates to systems and methods for remodeling soft tissue of a patient. More specifically, the present invention relates to drawing tissue portions toward one another to, for example, reduce or close body cavities or lumens, such as heart chambers, heart valves and other generally hollow anatomical structures.

Description of the Related Art

Several surgical techniques have been developed to close defects in tissue, reduce or close tubular structures, remodel cavities and repair bodily valves. However, the existing techniques require surgery or, even if non-invasive, suffer from significant drawbacks. For example, existing techniques may be generally difficult to perform, leave large residual foreign materials in the body, or not very effective in achieving the desired results.

For example, with respect to vascular or heart tissue remodeling, minimally invasive methods are fairly complex and often leave devices, such as stents, umbrellas, disks, plugs or rods, within a blood pathway of the body, which could promote thrombus formation. With respect to mitral or aortic regurgitation, minimally invasive methods typically insert a rod or similar apparatus within the coronary sinus. However, such a method could lead to erosion of the coronary sinus or other problems to the patient. Alternative devices and methods that attach the valve leaflets together to reduce regurgitation could lead to tears in the leaflets, which could require further surgery.

To properly and consistently repair the mitral valve, the following variables are relevant: the annular diameter, the leaflet length, the chordal length and the attachment point of the chords. Fortunately, the leaflet length is relatively constant. The annulus diameter can be fixed by the annuloplasty ring. The chords can be replaced by polytetrofluorethylene suture to fix their length. The missing variable is the attachment of the chords to the left ventricle. To date, this remains a troublesome variable to the valve repair.

Ischemic mitral regurgitation occurs when there is ventricular dysfunction which causes the posterolateral attachments of the mitral valve to be drawn away from the annulus in systole. This pulls the two leaflet edges apart at their point of coaptation and produces an asymmetrical regurgitate jet or, in other words, blood flow in the wrong direction through the valve. In an ideal situation, the leaflets, the chords and the attachment points are all anatomically normal. Sometimes there is a relative discrepancy between the distances the anterior leaflet is drawn inward relative to the posterior leaflet so they are not just separated from edge-to-edge but also there is a step deformity of the junction point. The patient may also have some underlying mild degree of degenerative deformity which may initially cause a mild, but well-tolerated degree of mitral regurgitation. However, the regurgitation often becomes severe after left ventricular ischemia occurs.

Some repair techniques apply tight annuloplasty rings which serve to buckle the leaflets and draw them together to, for example, correct ischemic disease. This often leaves a degree of mitral regurgitation and mitral stenosis results. However, long term results seem to degenerate after a couple of years due to the continuing of the dilation in the ventricle it self, which changes the attachment point position in regard of the annulus and by pulling on the chords, the leaflet edges will no longer coapt, thereby producing regurgitation. Accordingly, a need exists for improved minimally invasive tissue remodeling devices and methods in general, and particularly for the purpose of adjusting the location of the attachment of the chords to the left ventricle relative to the valve annulus.

SUMMARY OF THE INVENTION

Preferred systems and methods of the present invention permit remodeling of soft tissue structures using minimally invasive techniques, which preferably are catheter based. In many arrangements, the systems and methods leave little or no foreign objects within fluid pathways of the body. In certain preferred embodiments, a purse string device is placed within a body cavity or tubular structure to reduce or completely close the cavity or structure. The preferred systems and methods are well suited for use in structural defect repair, including treatment of heart valve insufficiency, heart ventricle remodeling, and closure of a vessel. In some arrangements, the purse string device may be a suture and, in other arrangements, the purse string device may be a coiled member.

A preferred method includes positioning a distal end of a catheter proximate a body structure and securing a plurality of anchors to tissue of the body structure comprising advancing a piercing member into a wall of the body structure by passing the member through an inner surface of the wall of the body structure. Tissue anchors are deployed from the piercing member such that at least a portion of the anchor contacts the outer surface of the wall of the body structure. A force is applied to a purse string to draw at least some of the anchors towards each other.

A preferred method includes providing a catheter comprising a plurality of tissue anchors and positioning a distal end of the catheter proximate a body structure. The plurality of tissue anchors are substantially simultaneously secured at respective spaced locations within the body structure. The securing comprises advancing a distal-most end of the catheter into contact with tissue at the spaced locations.

A preferred method includes providing a catheter comprising a guide catheter and a plurality of delivery catheters having a curved pre-shape and carrying respective tissue anchors. The delivery catheters are disposed within the guide catheter. A distal end of the catheter is positioned proximate a body structure. The plurality of tissue anchors are secured at respective spaced locations within the body structure by advancing the plurality of delivery catheters through the guide catheter such that distal end portions of the delivery catheters protrude from a distal end of the guide catheter. The securing comprises positioning the anchors at respective distal ends of the delivery catheters and allowing the distal portions of the delivery catheters to move towards the curved pre-shape as the distal portions of the delivery catheters are advanced.

A preferred method of closing a fallopian tube includes positioning a distal end of a catheter at a location within the fallopian tube. The catheter is used to secure respective tissue anchors at at least three spaced locations in a wall of the tube. At least some of the tissue anchors are relatively moved by applying a force to a purse string such that the locations are drawn towards each other.

A preferred method of closing a fallopian tube includes positioning a distal end of a catheter at a location within the fallopian tube. The catheter is used to secure respective tissue anchors at at least three spaced locations in a wall of the tube. A line is serially threaded through the tissue anchors. Respective portions of the line are drawn through at least some of the tissue anchors such that the locations are drawn towards each other.

A preferred method of repairing a heart valve includes introducing a distal end of a catheter through vasculature to a location proximate a heart valve. The catheter is used to secure respective tissue anchors at at least three spaced locations adjacent the valve. At least some of the tissue anchors are relatively moved by applying a force to a purse string such that the valve leaflets are repositioned to improve valve function.

A preferred method of repairing a heart valve includes introducing a distal end of a catheter through vasculature to a location proximate a heart valve. The catheter is used to secure respective tissue anchors at at least three spaced locations adjacent the valve. A line is serially threaded through the tissue anchors. Respective portions of the line are drawn through at least some of the tissue anchors such that the valve leaflets are repositioned to improve valve function.

A preferred method of reshaping a heart ventricle includes introducing a distal end of a catheter into the ventricle through vasculature. The catheter is used to secure respective tissue anchors at at least three spaced locations in a wall of the ventricle. At least some of the tissue anchors are relatively moved by applying a force to a purse string such that the ventricle is reshaped.

A preferred method of reshaping a heart ventricle includes introducing a distal end of a catheter into the ventricle through vasculature. The catheter is used to secure respective tissue anchors at at least three spaced locations in a wall of the ventricle. A line is serially threaded through the tissue anchors. Respective portions of the line are drawn through at least some of the tissue anchors such that the ventricle is reshaped.

A preferred apparatus includes a catheter comprising a purse string interconnected with a plurality of tissue anchors configured to be secured to one of heart tissue, blood vessel tissue, or fallopian tube tissue, such that, in use, force on the purse string moves at least some of the secured tissue anchors to reshape the heart, improve heart valve function, or close a fallopian tube, respectively.

A preferred method of repositioning leaflets of a mitral valve of a heart to improve valve function includes advancing a distal end of a catheter through an opening in the septal wall of the heart and into the left ventricle of the heart. A purse string is provided. The catheter is used to secure the purse string at a plurality of locations adjacent an inner surface of the wall of the ventricle. A force is applied to the purse string to alter the shape of the left ventricle such that the leaflets are repositioned to improve the function of the valve.

A preferred method of repositioning leaflets of a mitral valve of a heart to improve valve function includes providing a plurality of anchors in tissue of a wall of a ventricle such that at least some of the anchors are interconnected by an elastic member. The anchors are positioned such that the elastic member is in tension so as to elastically draw at least some of the anchors toward one another to alter the shape of the left ventricle such that the leaflets are repositioned to improve the function of the valve.

A preferred method of repositioning leaflets of a mitral valve of a heart to improve valve function include advancing a distal end of a catheter into a right chamber of the heart. The catheter is used to advance a line through the wall of the left ventricle in a direction parallel to inner and outer surfaces of the wall such that the line extends along the wall generally parallel to the surfaces substantially from a location on one side of the heart to a location on an opposite side of the heart. A force is applied to the line to alter the shape of the left ventricle such that the leaflets are repositioned to improve the function of the valve.

A preferred method of repositioning leaflets of a mitral valve of a heart to improve valve function includes advancing respective distal ends of first and second guide catheters into a right chamber of the heart and through respective spaced locations in the septal wall to the left ventricle. The guide catheters are used to facilitate positioning of an anchor positioning member in the left ventricle. The anchor positioning member is oriented so as to extend from one side of the ventricle to another. The anchor positioning member is used to secure a plurality of anchors to the wall of the ventricle by pressing the anchors against tissue. At least some of the anchors are drawn toward one another to alter the shape of the left ventricle such that the leaflets are repositioned to improve the function of the valve.

A preferred method of repositioning leaflets of a mitral valve of a heart to improve mitral valve function includes providing an elongate anchor positioning member and a series of anchor stowage members disposed serially in spaced relationship along the anchor positioning member. The elongate anchor positioning member is pressed against a wall of the ventricle such that the positioning member supports the stowage members adjacent the wall. Respective anchors are driven out of the stowage members and into ventricular tissue while the anchor positioning member supports the stowage members. The anchor positioning member is removed from the ventricle. A line interconnecting the anchors is used to apply force to the anchors and thereby alter the shape of the ventricle such that the leaflets are repositioned to improve valve function.

A preferred apparatus for altering the shape of a ventricle of a heart includes a catheter configured to be introduced into a heart chamber through vasculature. The catheter has a sharp distal end which bores through tissue so as to form a passage therethrough. The catheter also has a steering member which steers the sharp distal end through ventricular tissue generally parallel to inner and outer wall of the ventricle. The steering member is configured to follow the sharp distal end through the passage. The sharp distal end is connected to a line detachable from the distal end. The line is sized to extend through the passage such that tension on the line alters the shape of the ventricle.

A preferred apparatus for altering the shape of a ventricle of a heart includes an elongate anchor positioning member.

A plurality of anchor stowage members are disposed serially in spaced relationship along the anchor positioning member. A plurality of anchors stowed within respective anchor stowage members. The anchors are interconnected by a line. The anchor positioning member is configured to support the anchor stowage members adjacent to a ventricular wall. An actuator drives the anchors from the anchor stowage members into ventricular tissue while the anchor positioning member supports the anchor stowage members.

BRIEF DESCRIPTION OF THE DRAWINGS

These and other features, aspects and advantages of the present tissue remodeling devices and methods are described in greater detail below with reference to drawings of several preferred embodiments, which are intended to illustrate, but not to limit, the present invention. The drawings contain 48 figures.

FIG. 2 is a longitudinal cross-sectional view of a distal end of the catheter of FIG. 1.

FIGS. 3a and 3b are radial cross-section views of the catheter of FIG. 1 illustrating two alternative cross-sectional shapes of a delivery catheter of the catheter assembly.

FIG. 4 is a side view of the catheter of FIG. 1 contacting soft tissue of a patient. The catheter of FIG. 1 includes an inflatable balloon configured to provide an atraumatic tissue contact surface.

FIGS. 5a through 5f illustrate the catheter of FIG. 1 at various positions while being utilized to place tissue anchors at desired positions in the soft tissue of a patient.

FIGS. 6a and 6b illustrate the tissue anchors and a purse string being utilized to reduce the cross-sectional dimension of a body lumen, such as a blood vessel, for example. FIG. 6a illustrates the purse string device prior to the reduction of the cross-sectional dimension of the lumen and FIG. 6b illustrates the purse string device having been utilized to draw at least a portion of the tissue anchors towards one another to reduce the cross-sectional dimension of the lumen.

FIG. 7a illustrates the tissue anchors and purse string in place within the lumen prior to reduction of the cross-sectional dimension and FIG. 7b illustrates the tissue anchors and purse string after the purse string has been utilized to draw at least a portion of the tissue anchors towards one another to close the body lumen.

FIG. 11 shows the front, top and a first side of the tissue anchor in a relaxed or unconstrained position.

FIGS. 20a and 20b are views of the heart taken along the line 20-20 of FIG. 19.

FIG. 21 is a side view of another tissue remodeling system having certain features, aspects and advantages of the present invention. A distal end of the catheter assembly of FIG. 21 is illustrated in cross-section to reveal multiple delivery tubes within the guide catheter of FIG. 21.

FIG. 22 illustrates the distal end of the catheter assembly of FIG. 21 with the pre-curved delivery catheters deployed from the guide catheter.

FIG. 23 illustrates the distal end of the catheter of FIG. 21 with the delivery catheters deployed from the guide catheter and tissue anchors deployed from each of the delivery catheters. A line, such as a suture, interconnects each of the tissue anchors.

FIGS. 26a through 26e illustrate the catheter of FIG. 21 being utilized to remodel an aortic valve of a patient's heart.

FIG. 27 is a perspective view of another preferred tissue remodeling system including a catheter assembly having certain features, aspects and advantages of the present invention.

FIG. 28 is a longitudinal cross-sectional view of a distal end of the catheter of FIG. 27 illustrating a tissue anchor delivery catheter within a guide catheter.

FIG. 29 is an end view of a distal end of the guide catheter of FIG. 28.

FIG. 30 illustrates the catheter of FIG. 27 being utilized to deliver tissue anchors into soft tissue of a patient.

FIG. 31 is a perspective view of a preferred system for remodeling soft tissue of a patient including a catheter assembly. The catheter assembly includes a linear coil purse string device.

FIG. 32 is an enlarged view of the linear coil purse string device.

FIG. 33 illustrates the linear coil purse string device with multiple tissue anchors deployed therefrom.

FIG. 34 is an enlarged view of a tissue anchor stowage device carried by the linear coil purse string device.

FIG. 35 illustrates a deployment mechanism configured to deploy the tissue anchors from the tissue anchors stowage devices.

FIG. 36 illustrates a tissue anchor being deployed from the tissue anchor stowage device. In addition, FIG. 36 illustrates a support rod which is configured to hold the tissue anchor stowage devices at a desired position relative to one another prior to deployment of the tissue anchors. The support rod preferably is removed once the anchors are deployed to permit the linear coil purse string device to contract and thereby remodel soft tis sue.

DETAILED DESCRIPTION OF THE PREFERRED EMBODIMENTS

Preferred embodiments of the present tissue remodeling system facilitate remodeling, tissue joining, or tying of soft tissue preferably in a percutaneous manner utilizing a catheter. In certain preferred arrangements, the system permits a remodeling of the left ventricle of a heart to reduce the volume of the ventricle or reposition papillary muscles. In addition, the preferred systems may be utilized to remodel valve structures, such as the aortic or mitral valves of the heart. Certain systems and methods disclosed herein may be well-suited to treat Ischemic Mitral Regurgitation (IMR), for example. Further, preferred embodiments may be utilized to reduce the cross-sectional area of body cavities or lumens, or completely close body cavities or lumens. Preferred methods for remodeling soft tissue are also disclosed.

Preferably, the preferred embodiments permit soft tissue remodeling while avoiding the disadvantages of more invasive procedures and the complications that may occur as a result of such procedures. The preferred embodiments and methods may also permit tissue remodeling in patients that are otherwise unable to undergo conventional surgical procedures. Preferred embodiments of the present system permit the duplication of the results of surgical procedures by percutaneous transvascular techniques using catheter-based devices. In addition, the preferred embodiments and methods disclosed herein maybe modified or adopted for use in the remodeling of soft tissue other than the heart or body lumens. Preferably, the methods described herein are accomplished with a suitable imaging technique, or techniques, such as transesophageal echocardiogram (TEE), angiographic fluoroscopy or cineangiographic guidance, for example.

Figure 1:
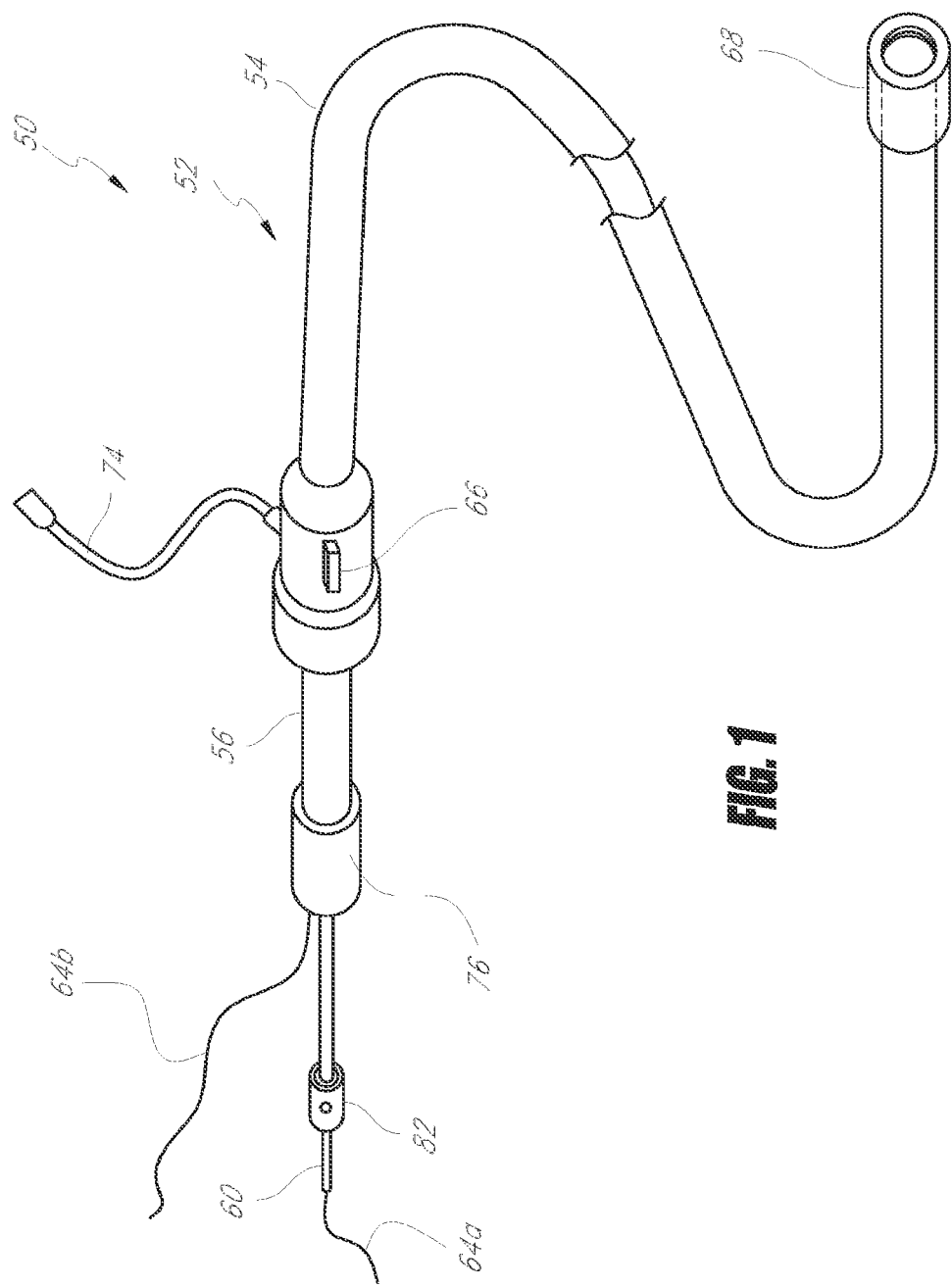
FIG. 1 is a perspective view of a tissue remodeling system having certain features, aspects and advantages of the present invention. The tissue remodeling system of FIG. 1 includes a catheter assembly including several coaxial catheter bodies.

FIGS. 1-3 illustrate a tissue remodeling system having certain features, aspects and advantages of the present invention and is generally referred to by the reference numeral 50. The illustrated system 50 includes a catheter assembly 52, which preferably includes multiple catheters, or catheter bodies. For simplicity, both the overall catheter assembly 52 and the individual catheter bodies that make up the catheter assembly 52 may be referred to herein by the term "catheter." Furthermore, the catheter 52 may include other components as well, such as tissue anchors, for example. Preferably, the catheter 52 is sized, shaped and otherwise configured to be movable within a patient's vasculature to a desired remodeling site from a desired insertion site. In some arrangements, the insertion site may be the femoral artery, for example. However, other suitable insertion sites may also be used.

Preferably, the catheter 52 includes multiple components that are coaxial with one another and are capable of telescopic movement relative to one another. In the illustrated arrangement, the catheter assembly 52 includes a guide catheter 54. A delivery catheter 56 is configured to be received within the guide catheter 54 and is movable relative to the guide catheter 54. A tissue piercing or penetrating member, such as a needle 58, is received within, and is movable relative to, the delivery catheter 56, as shown in FIG. 2. A pushing mechanism, such as a push rod 60, is received within, and movable relative to, the needle 58 and may be used to deploy tissue anchors 62 (FIG. 2) from the needle 58, as is described in greater below. A line, such as a suture 64, extends through the needle 58, interconnects the anchors 62 and extends back through the delivery catheter 56 such that both ends 64a and 64b of the suture 64 are external of the proximal end of the catheter assembly 52.

The individual components of the catheter assembly 52 may be constructed from any suitable material(s) using any suitable fabrication techniques, such as those commonly known and used in the medical device industry. For example, the guide catheter 54 and delivery catheter 56 maybe constructed from a suitable polymeric material, such as polyethylene, polyurethane, silicon, or polytetraflouroethylene, for example. The catheters 54 and 56 may be constructed by an extrusion process; however, other suitable materials and/or suitable processes may be used. The needle 58 and push rod 60 preferably are constructed from a metal material suitable for use in medical applications, such as stainless steel or a shape-memory material, for example. However, other suitable materials and/or suitable fabrication processes may also be used.

As described above, the guide catheter 54 preferably is configured to be introduced to the patient's vasculature at an introduction site and guided through the vasculature through the desired working site, such as the heart, for example. Thus, preferably, the guide catheter 54 is of a sufficient length such that the distal end of the catheter 54 may reach the desired work site while the proximal end of the catheter 54 remains external of the patient. The guide catheter 54 may have an outer diameter of about 26F (French) and an inner (lumen) diameter of about 22F. However, other dimensions may be employed depending on the specific use of the catheter 54, as will be appreciated by one of skill in the art.

Preferably, the guide catheter 54 is configured to be steerable to permit the catheter 54 to be guided through vasculature to the desired work site or to be steerable once at the work site. For example, a deflection wire (not shown) may be connected to a distal end of the guide catheter 54 and extend within a wall of the catheter 54 to a proximal end of the catheter 54 where it is connected to a control knob 66. Thus, the control knob 66 permits the user to selectively push or pull the deflection wire to deflect the distal end of the guide catheter 54. Deflection of the distal end of the guide catheter 54 assists a user in routing the catheter 54 through the vasculature of a patient in a desired path or position the distal end of the catheter 54 once at the work site. Such a system is disclosed in greater detail in the applicant's co-pending U.S. patent application Ser. No. 11/059,866, filed Feb. 17, 2005 and entitled "Catheter Based Tissue Remodeling Devices and Methods," the entirety of which is incorporated by reference herein. Alternatively, other suitable steering arrangements or positioning methods of the guide catheter 54 may be employed. In one arrangement, the guide catheter 54 may be configured to slide over a previously placed guide wire (not shown) or may be passed through a previously placed catheter.

Preferably, the distal end of the guide catheter 54 is configured to be atraumatic to the patient and, in particular, to the tissue proximate the work site. In the illustrated arrangement, the distal tip of the guide catheter 54 carries an inflatable, preferably annular balloon 68. Preferably, the balloon 68 is normally carried by the guide catheter 54 in an uninflated condition so as not to interfere with the passage of the catheter 54 through a patient's vasculature. Once in place at or near the work site, the balloon 68 may be inflated such that a distal end of the balloon 68 contacts the patient's soft tissue to help stabilize the catheter 54 and inhibit the distal tip of the catheter 54 from damaging tissue. Preferably, the balloon 68, in an inflated condition, extends beyond an end surface of the distal end of the catheter 54 to create a space 70 between the distal end of the catheter 54 and the tissue 72, as illustrated in FIG. 4.

The balloon 68 may be constructed from any suitable material, such as silicon, urethane, Pebax, polyimide and multi-layered polymers, for example. The balloon 68 may be inflated by a suitable fluid, including liquid or gas. Preferably, a passage (not shown) extends from a proximal end of the catheter 54 to an internal space of the balloon 68 so that an inflation fluid may be introduced into the balloon 68 from the proximal end of the catheter 54. The passage may be defined within the body of the catheter 54 or may be formed by a separate element of the catheter assembly 52.

Desirably, the catheter assembly 52 also includes a system for creating a vacuum within the space 70 bounded by the balloon 68. The catheter assembly 52 includes a conduit, or tube 74, which is configured to be connectable to a vacuum pump (not shown). The tube 74 communicates with a passage preferably within the catheter body of the catheter 54 (not shown) which, in turn, communicates with the space 70. Thus, the vacuum pump may be operated to produce a vacuum condition within the space 70 to assist in securing the distal end of the catheter 54 at a desired location on the patient's tissue 72. Alternatively, the vacuum passage may be created by a component of the catheter assembly 52 other than the guide catheter 54.

As described above, the delivery catheter 56 is configured to reside within the guide catheter 54 and is capable of movement within the guide catheter 54. The delivery catheter 56 may have an outer diameter of about 18F and an inner (lumen) diameter of about 13F. However, other dimensions may be selected to suit a desired application of the catheter 56. The delivery catheter 56 may be constructed of any suitable material or combination of materials, such as polyethylene, polyurethane, silicone or polytetraflouroethylene, for example. Desirably, a proximal end of the catheter 56 includes a handle 76, or hub, which permits a user to grasp and manipulate the catheter 56.

With reference to FIGS. 3a and 3b, the delivery catheter 56 may take on any suitable cross-sectional shape. As described above, the delivery catheter 56 is configured to receive the needle 58. In addition, desirably, a length of the suture 64 extends through the delivery catheter 56 external of the needle 58. To accommodate both the needle 58 and the suture 64, preferably the lumen of the catheter 56 defines a generally circular space 78 to accommodate the needle 58 and an additional space 80 configured to accommodate the suture 64 adjacent the space 78. As illustrated in FIG. 3a, in one arrangement, the space 80 may be connected to the space 78 or, as illustrated in FIG. 3b, the space 80 may be defined by a separate lumen of the catheter 56.

The needle 58 preferably is configured to stow the tissue anchors 62 and a portion of the suture 64 and facilitate the deployment of the tissue anchors 62 and suture 64. Similar to the delivery catheter 56, the needle 58 preferably includes a handle, or hub 82, at its proximal end to permit a user to manipulate the needle 58. Furthermore, preferably, a distal tip 84 of the needle 58 is beveled to facilitate tissue penetration. In one preferred arrangement, the needle 58 is constructed from a shape-memory material, such as Nitinol, for example, to provide a beneficial degree of flexibility. However, other suitable materials may also be used, such as stainless steel, for example. Further, the needle 58 could be of a composite construction to permit the optimization of certain characteristics, such as needle penetration and shaft flexibility, for example. The hub 82 may be constructed from a plastic or metal material, for example, through any suitable process, such as molding or machining.

The suture 64 may also be constructed of any suitable material. For example, preferably the material is non-bioabsorbable. However, in certain arrangements, the suture 64 may be constructed from a bioabsorbable material, if desired. Further, the material may be monofilament or multifilament, single strand or braided and a natural material or a synthetic material. Suitable materials may include Polyglactin (e.g., coated vicryl), Polydioxanone (PDS), Polyamide or Nylon (e.g., ETHILON), Polyester (DACRON) or Polypropylene (PROLENE), among others.

FIGS. 5a-5f illustrate a preferred method of using the system 50 to deliver tissue anchors that are interconnected by a line, such as the suture 64, to the soft tissue 72 of a patient. In FIGS. 5*a*-5*f*, the guide catheter 54 has been omitted for the purpose of clarity. However, preferably the guide catheter 54 is placed against the tissue 72 as described above with reference to FIG. 4.

FIG. 5*a* illustrates the needle 58 in suture 64 stowed within the delivery catheter 56. Accordingly, the needle 58 and suture 64 do not protrude from a distal end of the delivery catheter 56. FIG. 5*b* illustrates the delivery catheter spaced a slight distance from the soft tissue 72 of the patient. The needle 58 is advanced from the delivery catheter 56 and carries the suture 64 with it. In FIG. 5*c*, the delivery catheter 56 is advanced until it contacts the tissue 72. In addition, the needle 58 is advanced through the tissue 72, bringing the suture 64 along with it. The movement of the delivery catheter 56 into contact with the tissue 72 and the movement of the needle 58 through the tissue 72 maybe performed in any order, or simultaneously, if desired.

In FIG. 5*d*, the tissue anchor 62 is illustrated in the process of being deployed from the needle 58. As is shown in FIG. 5*d*, the suture 64 extends through an eyelet 62*a* of the tissue anchor 62. Although not illustrated, preferably the tissue anchor 62 is deployed from an end of the needle 58 due to the advancement of the push rod 60. Specifically, the push rod 60 may be used to exert a pushing force on the proximal most tissue anchor 62, which is transferred through the stack of tissue anchors 62 within the needle 58 to deploy the distal most tissue anchor 62.

Once deployed, preferably the tissue anchor 62 is positioned on the opposite side of the tissue 72 from the delivery catheter 56 and the suture 64 extends through the hole in the tissue 72 created by the passage of the needle 58 through the tissue 72. Thus, when tension is applied to the suture 64, the tissue anchor contacts the surface of the tissue 72 opposite the catheter 52, which may be the outside surface of the heart chamber or vessel, for example. However, in other arrangements, the tissue anchor may be configured to reside within the tissue 72 and, accordingly, the delivery catheter 58 may not be passed completely through the tissue 72 before the anchor is deployed.

As illustrated in FIG. 5*e*, once the tissue anchor 62 has been deployed, the needle 58 may be retracted into the delivery catheter 56. Both the needle 58 and delivery catheter 56 may be retracted within the guide catheter 54 and away from the tissue 72.

With reference to FIG. 5*f*, preferably, the catheter 52 is moved along the tissue a desired distance D from the first tissue anchor 62 and another tissue anchor 62 is deployed, preferably by the same or a similar method. This process is repeated until a desired number of tissue anchor 62 have been deployed. The distance D may be modified as desired to suit an individual application. For example, for remodeling a lumen, preferably the distance D is adjusted such that preferably at least three and, more preferably, about 3 to 10 tissue anchors 62 may be implanted.

FIGS. 6*a* and 6*b* illustrate multiple tissue anchors 62 interconnected by a line, such as the suture 64, which may be utilized to reduce the cross-sectional dimension of a tissue wall 90 that defines a cavity or lumen 92. As illustrated, the tissue anchors 62 are positioned at desired space locations around the circumference of the tissue wall 90 and interconnected by the suture 64. With such an arrangement, desirably, very little foreign material is placed across the lumen such that blood flow is left relatively or substantially completely undisturbed.

Preferably, the tissue anchors 62 are generally positioned within a single plane. However, other suture placement orientations may also be used. Tension may be applied to one or both of the ends 64*a*, 64*b* of the suture 64 to draw the tissue anchors 62 towards one another. As a result, the cross-sectional dimension of the tissue wall 90 is reduced, as illustrated in FIG. 6*b*. The suture ends 64*a*, 64*b* may then be secured together to secure the tissue wall 90 in a reduced configuration. For example, in one arrangement, the ends 64*a* and 64*b* may be tied in a knot 94. The knot 94 may be created outside of the catheter 52 and advanced through the catheter by any suitable method, such as by a conventional knot pusher or other suitable instrument, for example. Alternatively, the ends 64*a*, 64*b* may be secured to one another by a suitable connector.

Figure 7A:
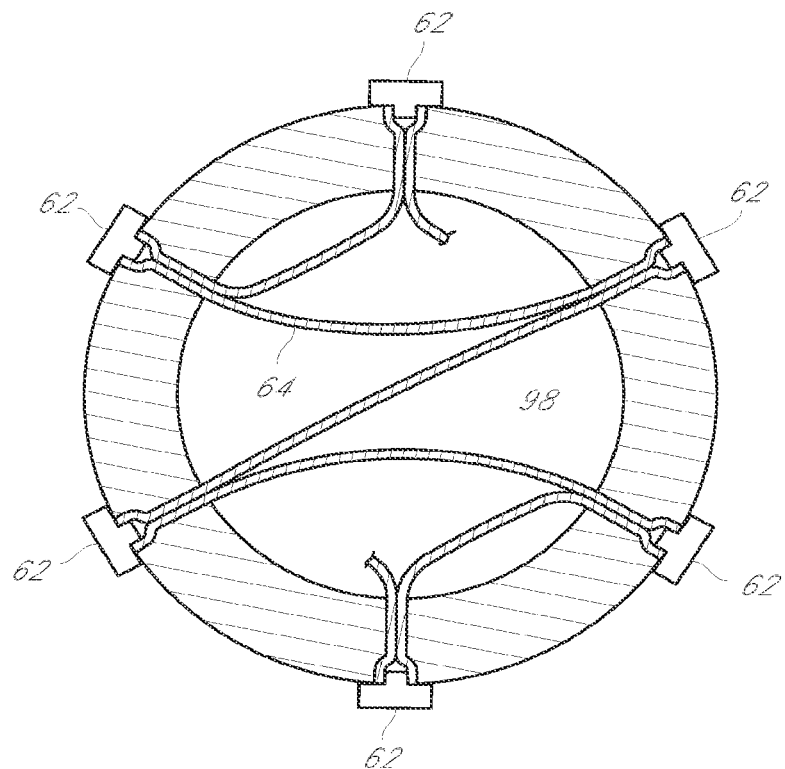
FIGS. 7a and 7b illustrate the tissue anchors and purse string being utilized to close the body lumen, such as a fallopian tube, for example.
Figure 7B:
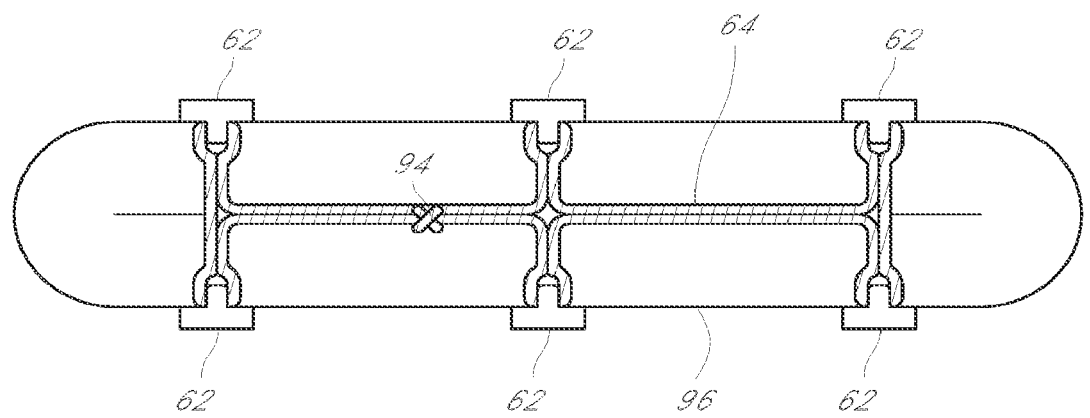

FIGS. 7*a* and 7*b* illustrate a plurality of tissue anchors 62 interconnected by a suture 64 and used to fold tissue or, more specifically in the illustrated arrangement, to collapse a wall of tissue 96 which defines a cavity or lumen 98 and, thus, reduce or close the lumen 98. In FIGS. 7*a* and 7*b*, instead of being placed sequentially around the circumference of the tissue wall 96, the tissue anchors 62 are placed in a non-serial manner. Preferably, the tissue anchors 62 are positioned generally across the tissue wall 96 from the previously placed tissue anchor 62 and, in some cases, even directly across from one another such that the suture 64 extends across the lumen or cavity 98. Accordingly, when one or both of the ends 64*a*, 64*b* of the suture 64 are pulled, the tissue wall 96 is collapsed onto itself. In a similar manner to that described above, the suture ends 62*a*, 62*b* may be secured to one another, such as by a knot 94, for example. Such a method is well-suited for tubal ligation, such as closing a fallopian tube, for example.

Figure 8A:
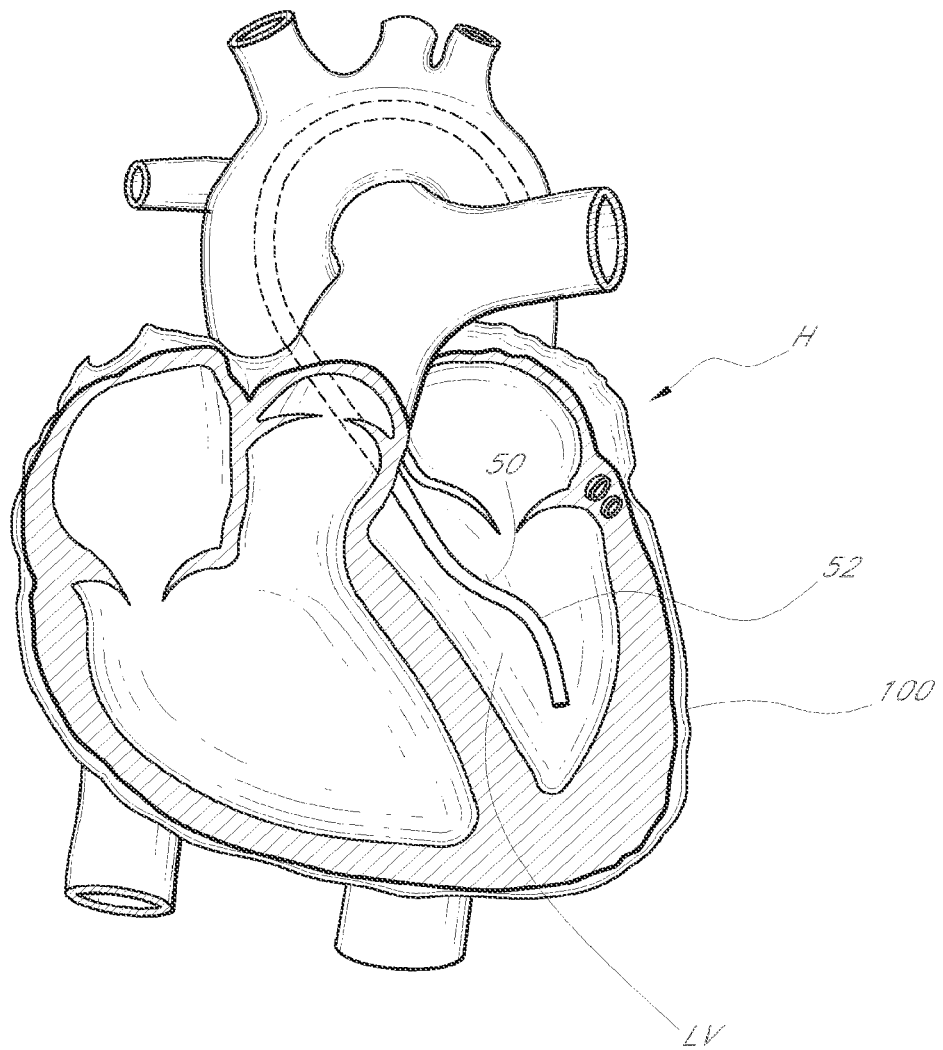
FIGS. 8a through 8c illustrate the catheter of FIG. 1 being utilized to deliver multiple purse string devices within the left ventricle of a patient's heart. The multiple purse string devices may be used to remodel, or reduce the volume, of the left ventricle to treat, for example, congestive heart failure. The devices may be used to remodel other heart chambers and other bodily cavities, as well.
Figure 8C:
Figure 8B:
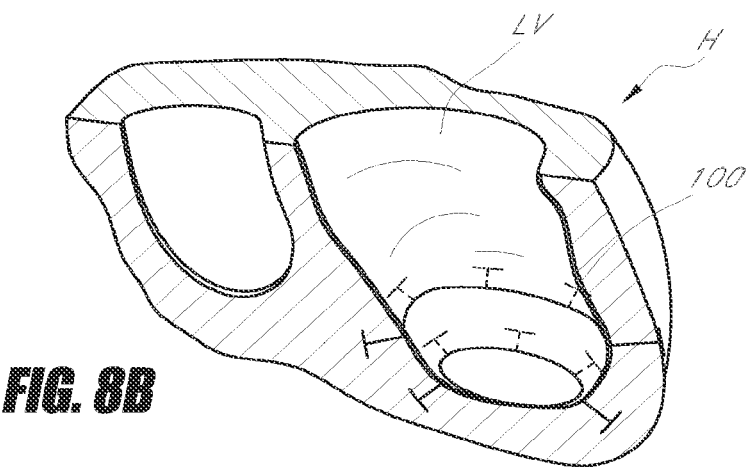

FIGS. 8*a*-8*c* illustrate the system 50 being utilized to reduce the volume of the left ventricle LV of a patient's heart H. In the illustrated arrangement, multiple rows of tissue anchors 62 are positioned within the wall 100 of the heart H surrounding the left ventricle LV. Preferably, each row of tissue anchors 62 includes its own suture 64 and, thus, each suture row may be tightened to a desired cross-sectional dimension separate from the other rows of tissue anchors 62. The tissue anchors 62 may be configured to be passed completely through the wall 100 to contact an external surface of the wall 100 or may be embedded within the tissue wall 100, as desired or necessitated by the tissue structure being remodeled. Such an arrangement provides essentially an internal basket structure, which preferably is delivered by a percutaneous transvascular approach, thus providing the benefits of a conventional compression device while avoiding the disadvantages of a conventional surgical procedure. The rows of implanted sutures 64 preferably limit a maximum expanded dimension of the ventricle LV, but do not limit compression. Adjustment of the suture tension or length, and thus the maximum dimension, may be based on feedback from the ejection fraction measurement of the ventricle, for example.

Figure 9:
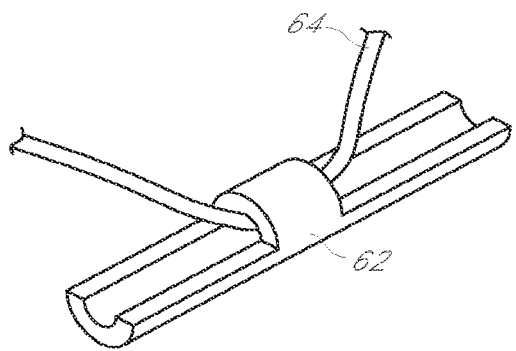
FIG. 9 is a perspective view of one preferred tissue anchor.
Figure 10:
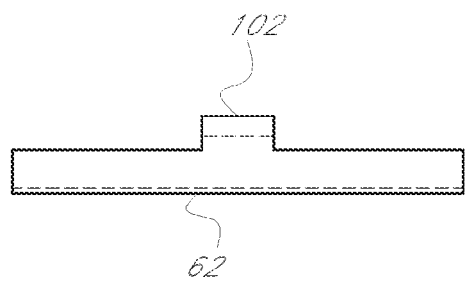
FIG. 10 is a side view of the tissue anchor of FIG. 9.

FIGS. 9 and 10 illustrate a preferred embodiment of a tissue anchor 62 that may be used in the system 50 described above, or the other systems described herein. In the illustrated arrangement, the tissue anchor 62 is constructed from a generally tubular element. A semi-cylindrical section of the tubular element is removed from each end, leaving an intermediate portion of the tissue anchor 62 defining an annular loop. The intermediate section of the tissue anchor 62 thus forms an eyelet 102 of the tissue anchor 62. Accordingly, the suture 64 may be passed through the eyelet 102, with the portions of the tissue anchor 62, on either side of the eyelet 102 configured to contact the soft tissue and prevent the tissue anchor 62 from being pulled through the passage in the tissue through which it was passed.

Figure 11:
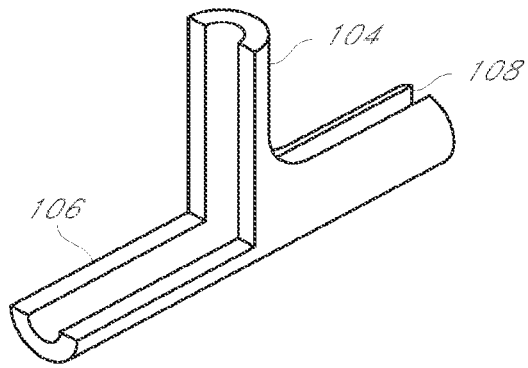
FIG. 11 is a perspective view of a modification of the tissue anchor of FIGS. 9 and 10.
Figure 13:
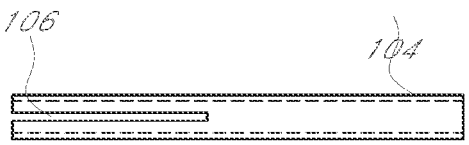
FIG. 13 illustrates the tissue anchor of FIGS. 11 and 12 in a collapsed or constrained position.
Figure 14:
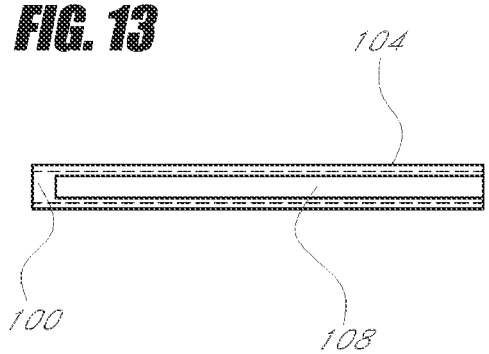
FIG. 14 is another view of the tissue anchor of FIGS. 11 and 12 in the collapsed position and rotated about its longitudinal axis by approximately ninety degrees from the view of FIG. 13.
Figure 12:
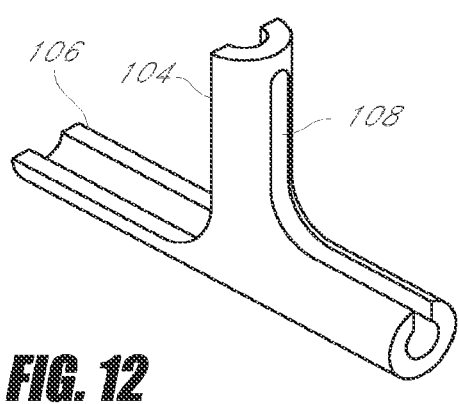
FIG. 12 is a perspective view of the tissue anchor of FIG. 11 illustrating the front, top and a second side of the tissue anchor, opposite the side from FIG. 1.

FIGS. 11-14 illustrate another preferred embodiment of a tissue anchor, generally referred to by the reference numeral 104. FIGS. 11 and 12 illustrate the tissue anchor 104 in an expanded configuration, while FIGS. 13 and 14 illustrate the tissue anchor 104 in a collapsed position. With reference to FIG. 13, the tissue anchor 104 preferably is constructed from a tubular element that includes a first slot 106 which extends from a first end of the element toward an intermediate portion of the element and generally bisects the tubular element. Preferably, the slot 106 extends about one-half the length of the tissue anchor 104 and, preferably, is aligned with the central axis of the tissue anchor 104.

With reference to FIG. 14, preferably a second slot 108 extends from a second end of the tissue anchor 104 preferably substantially the entire length of the tissue anchor 104 but terminates prior to the end of the tissue anchor 104 to leave a portion of material 110 at the first end of the tissue anchor 104. Preferably, the slot 108 is rotated on the tubular element from the slot 106 and, preferably, is located approximately 90 degrees about the central axis of the tissue anchor 104 from the slot 106. Furthermore, preferably the slot 108 passes only once through the wall of the tubular element.

Desirably, the tissue anchor 104 is constructed from a super-elastic, or shape-memory material, such as Nitinol, for example. However, other suitable materials may be used. Preferably, the tissue anchor 104 is heat set in the expanded position as illustrated in FIGS. 11 and 12, wherein a portion of the tubular element on one side of the slot 106 is bent away from the portion of the other side of the slot 106 until it is generally perpendicular to the remainder of the tubular element. Accordingly, in the absence of a biasing force, the tissue anchor 104 tends to assume the orientation shown in FIGS. 11 and 12. Preferably, the portion that is bent includes the slot 108 such that the slot 108 may function as an eyelet of the tissue anchor 104.

Figure 15:
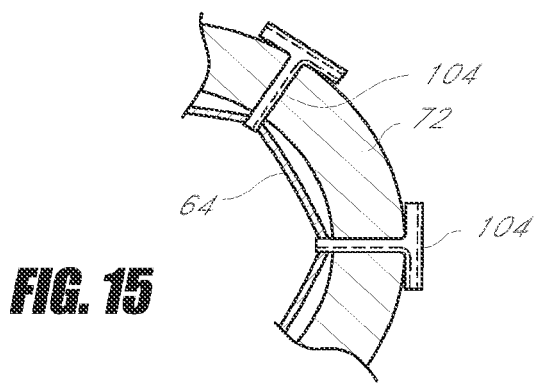
FIG. 15 illustrates a pair of the tissue anchors of FIGS. 11 through 14 implanted within soft tissue of a patient and interconnected by a line, such as a suture, for example.

Preferably, the tissue anchor 104 may be constrained, such as by the needle 58, into the orientation illustrated in FIGS. 13 and 14, or a collapsed orientation, so that the tissue anchors 104 may be delivered through tissue 72. As illustrated in FIG. 15, the tissue anchors 104 may be deployed in a similar manner to the tissue anchor 62 described above. However, once deployed, preferably the bent portion of the tissue anchor 104 including the slot 108 extends partially or completely through the tissue 72. Furthermore, the suture 64 may be passed through the slot 108 such that, when tension is applied to the suture 64, the tissue anchor 104 applies a force to the surface of the tissue 72 opposite the suture 64. With such an arrangement, adjustment of the suture 64 will likely be less affected by friction in comparison to the tissue anchors described above because the suture 64 does not pass through tissue.

Figure 16A:
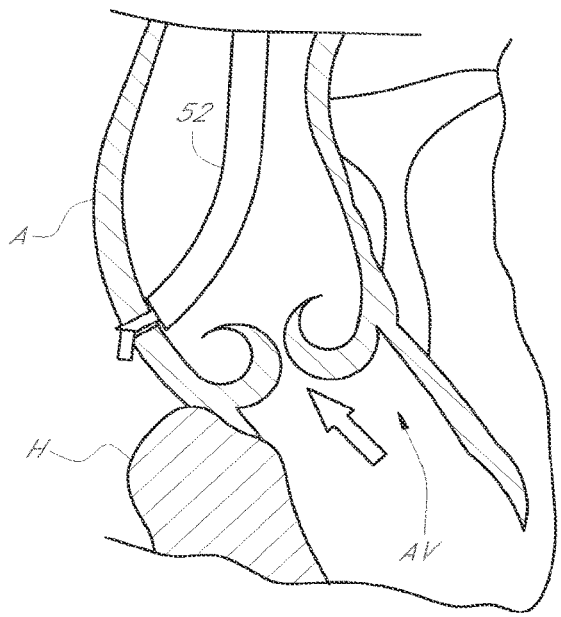
FIGS. 16a and 16b illustrate the catheter of FIG. 1 being utilized to remodel an aortic valve of a patient's heart.
Figure 16B:
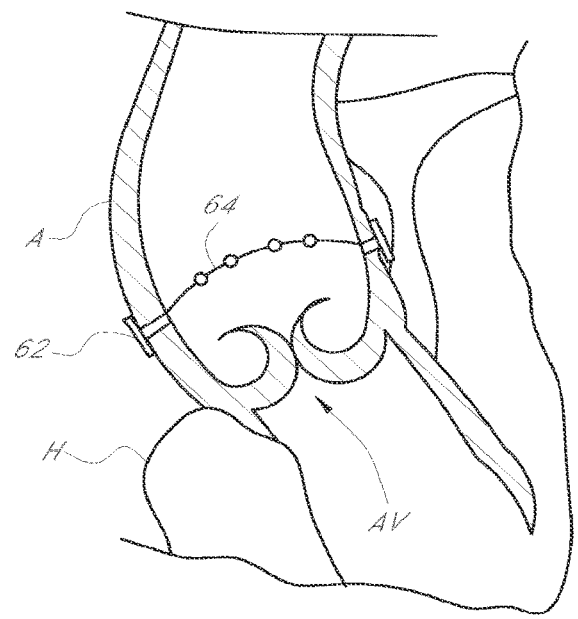

The above-described system 50 maybe utilized for a number of tissue remodeling applications. For example, with reference to FIGS. 16a and 16b, the system 50 may be utilized to remodel the aortic valve AV of a patient's heart H. That is, the catheter 52 may be used to place a number of tissue anchors 62 (or 104) within the aorta A and, preferably, at a location adjacent to the aortic valve AV. In the illustrated method, the guide catheter 54 may be omitted from the catheter assembly 52 and the delivery catheter 56 may be steerable. As described above, the tissue anchors 62 may be interconnected with a line, such as suture 64. Tension applied to the suture 64 draws the tissue anchors 62 towards one another to reduce the cross-sectional dimension of the aorta A. Accordingly, the leaflets of the aortic valve AV may be remodeled and, preferably, brought towards one another to reduce regurgitation through the valve AV. In the illustrated arrangement, the tissue anchors 62 are disposed on a downstream side of the valve AV. In addition, although only one row of tissue anchors 62 are illustrated, additional rows may be provided.

Figure 17A:
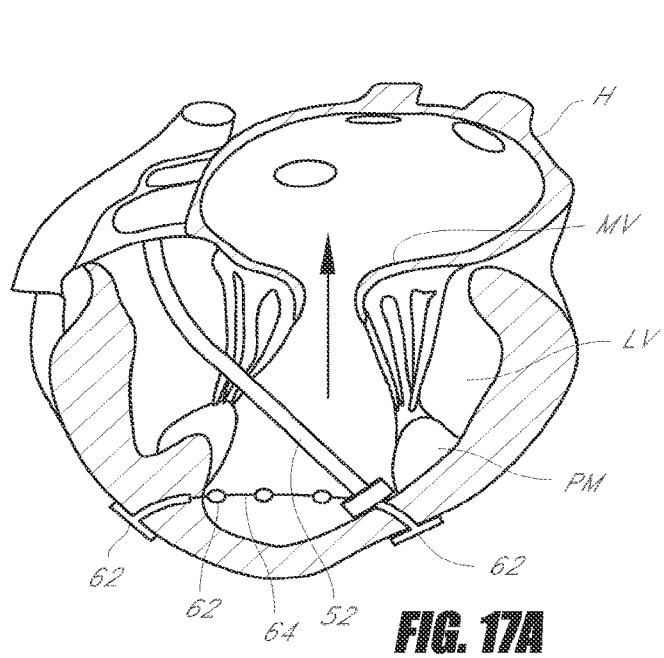
FIGS. 17a and 17b illustrate the catheter of FIG. 1 being utilized to remodel the mitral valve of a patient's heart. Specifically, in FIGS. 17a and 17b, the catheter is utilized to place a plurality of tissue anchors interconnected by a purse string device within a wall of the left ventricle to reposition the papillary muscles and, thus, the mitral valve leaflets.
Figure 17B:
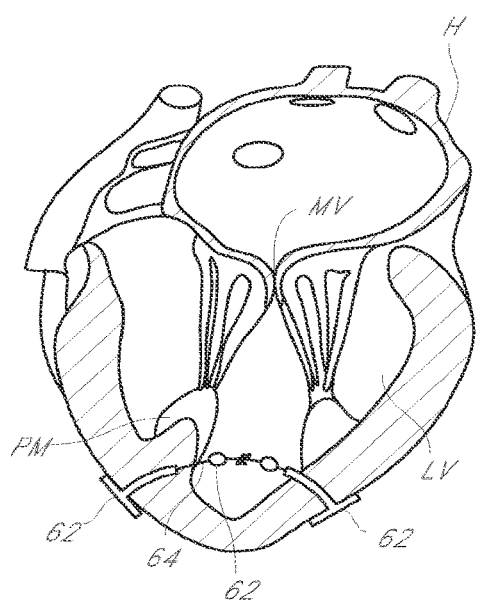

With reference to FIGS. 17a and 17b, the system 50 also may be utilized to remodel the left ventricle LV to improve the function of the mitral valve MV. For example, a plurality of tissue anchors 62 (or 104) may be positioned in a row in a generally circular manner proximate the papillary muscles PM, which are connected to the leaflets of the mitral valve MV. The tissue anchors 62 may be interconnected by a line, such as the suture 64, and tension applied to the suture 64 to draw the tissue anchors 62 towards one another. As a result, the papillary muscles PM may be drawn toward one another so that the leaflets of the mitral valve move toward one another, preferably until the leaflets properly coapt to reduce or eliminate regurgitation.

Figure 20A:
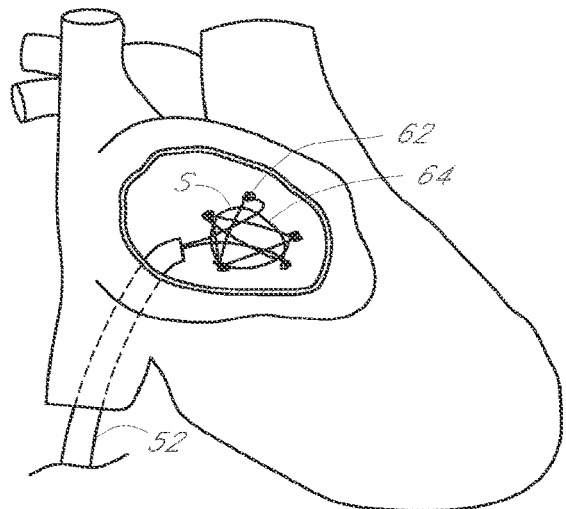
FIGS. 20a and 20b illustrate the catheter of FIG. 1 being utilized to repair the PFO.
Figure 19:
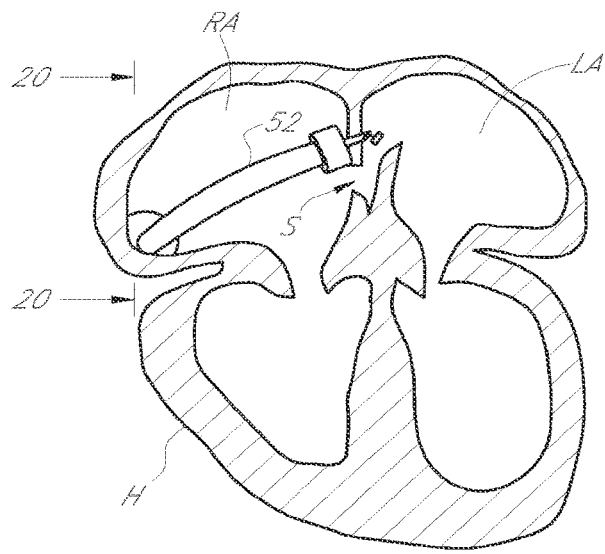
FIG. 19 illustrates the catheter of FIG. 1 being utilized to close the PFO of a patient's heart.
Figure 20B:
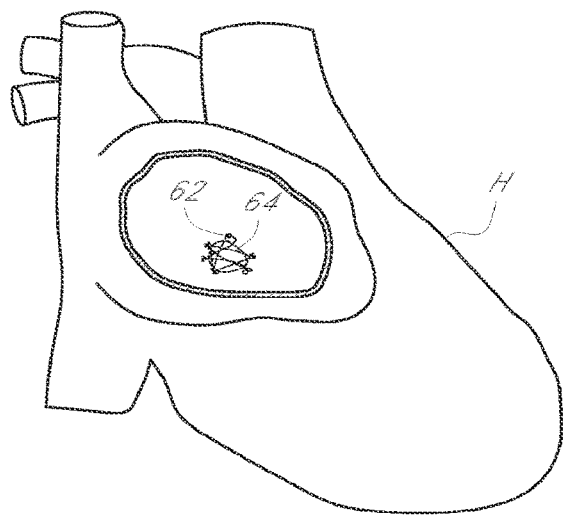
Figure 18:
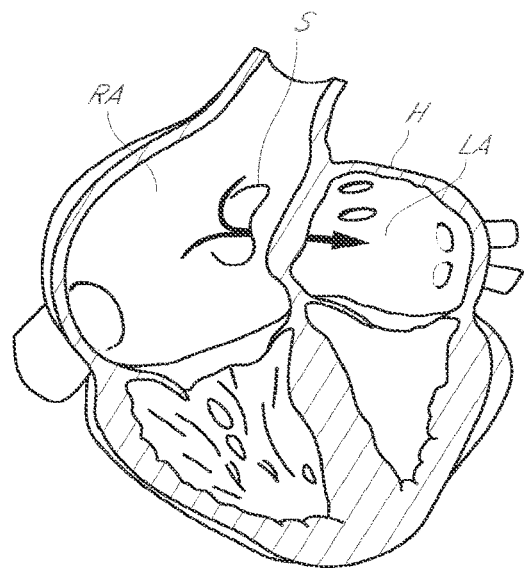
FIG. 18 is a cross-sectional view of a heart including an opening in an internal wall of the heart between the right atrium and left atrium, which is often referred to as a PFO (patent foramen ovale).

With reference to FIGS. 18-20, the system 50 may be utilized to repair a defect, or hole, within a patient's heart H. With reference to FIG. 18, a septal defect S, such as a patent foramen *ovale* (PFO), is illustrated in a heart H and, generally, is a hole in the septal wall between the right atrium RA and the left atrium LA. FIG. 19 illustrates the system 50 being used to place a plurality of tissue anchors 62 around the septal defect S. FIGS. 20a and 20b illustrate another view of the system 50 being utilized to close the septal defect S before and after tightening of the suture 64, respectively.

FIGS. 21-25 illustrate another system having certain features, aspects, and advantages of the present invention and generally referred to by the reference numeral 150. Similar to the system 50 described above, the system 150 is configured to deliver a plurality of tissue anchors to soft tissue of a patient. The tissue anchors preferably are interconnected by a line, such as a suture. However, rather than deploying the tissue anchors one at a time, preferably the system 150 is configured to deliver a plurality of tissue anchors simultaneously or substantially simultaneously.

The system 150 includes a catheter assembly 152, which preferably includes a guide catheter 154 and plurality of delivery tubes 156. The delivery tubes 156 are movable within the guide catheter 154 from a stowed position (FIG. 21) to a deployed position (FIGS. 22 and 23). Each of the delivery tubes 156 function in a manner similar to the delivery catheter 56 described above, or the other delivery catheters described herein. Thus, the collection of deliver tubes 156 essentially function as a plurality of delivery catheters, but preferably are sized such that multiple tubes 156 may be carried within the guide catheter 154. Preferably, each delivery tube 156 stows a tissue anchor 158. The tissue anchors 158 preferably are interconnected by a line, such as a suture 160.

Desirably, the guide catheter 154 is substantially similar to the guide catheter 54 of FIGS. 1-3. A proximal end of the guide catheter 154 defines a handle portion, or hub 162, which permits a user of the system 150 to manipulate the guide catheter 154. The guide catheter 154 may also be steerable in a manner similar to that described above in connection with the guide catheter 54 or by any other suitable arrangement. Preferably, the guide catheter 154 is sized such that the lumen is capable of accommodating a desired number of delivery tubes 156. In one arrangement, the guide catheter 154 may have a lumen diameter of about 20 to 24F. However, other suitable dimensions are also possible, depending on the specific application or number of delivery tubes 156 desired. In one arrangement, preferably between about 3 and 18 delivery tubes 156 are provided. More preferably, between about 8 and 12 delivery tubes 156 are provided for applications involving remodeling of the aortic valve AV. The guide catheter 154 may be constructed of any suitable material(s), such as those described above. If desired, the guide catheter 154 could include a braided material, or be otherwise manipulated, to increase axial or radial stiffness.

Preferably, the delivery tubes 156 are movable within the guide catheter 154. The delivery tubes 156 are secured to a proximal handle, or hub 164, which permits a user of the system 150 to move the plurality of delivery tubes 156 in an axial direction relative to the guide catheter 154 substantially simultaneously. Preferably, the delivery tubes 156 extend through the guide catheter 154 and are interconnected at the hub 164. However, in an alternative arrangement, the delivery tubes 156 may be coupled to the hub 164 by an intermediate component or components.

Desirably, each of the delivery tubes 156 has a curved distal end 166 when deployed from the guide catheter 154. The curved distal end 166 extends radially outward from a longitudinal axis of the guide catheter 154 preferably such that the distal end surfaces of the delivery catheters face in a direction generally perpendicular to the longitudinal axis of the guide catheter 154. Preferably, the curved distal ends 166 are preshaped such that the distal ends 166 of the delivery tubes 156 tend to move toward their curved configuration when no restraining force is present. When stowed within the guide catheter 154, the distal ends 166 of the delivery tubes 156 are restrained in a generally linear configuration and move to the precurved configuration when the delivery tubes 156 are deployed from the guide catheter 154. Preferably, the delivery tubes 156 are constructed of a super-elastic or shape-memory material that is manipulated to have the desired curvature at the distal end 166, as will be appreciated by one of skill in the art.

The distal ends 166 of the delivery tubes 156 are configured to stow at least one tissue anchor 158. In the illustrated arrangement, each of the distal ends 166 of the delivery tubes 156 include a slot 168 extending in an axial direction along the delivery tube 156. The slot 168 accommodates the suture 160 in interconnecting the tissue anchors 158 while in their stowed position within the delivery tubes 156. However, in other arrangements, the slots 168 may be omitted and the suture 160 may enter through the distal end of the lumen of the delivery tubes 156. Further, multiple tissue anchors 158 may be provided, if desired.

Figure 24:
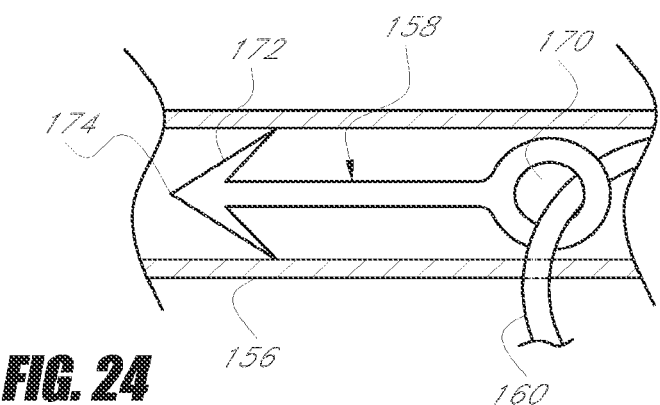
FIG. 24 is an enlarged view of a preferred embodiment of a tissue anchor within a delivery catheter of the catheter assembly of FIG. 21.
Figure 25:
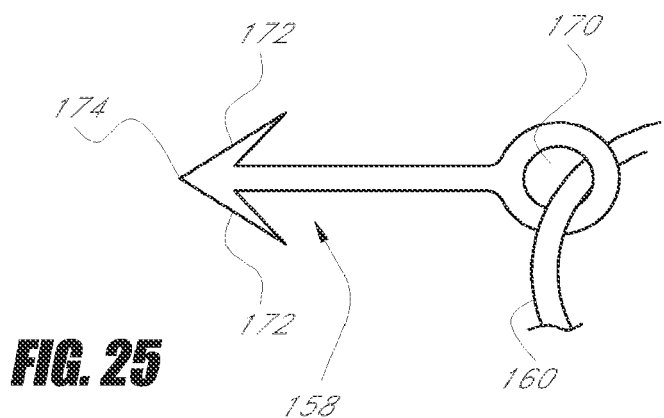
FIG. 25 illustrates the tissue anchor of FIG. 24 deployed from the delivery catheter.

FIGS. 24 and 25 illustrate one preferred tissue anchor 158 in stowed and deployed orientations, respectively. Desirably, the tissue anchor 158 includes an eyelet 170 at its proximal end and a pair of barbs 172 at its distal end. Preferably, the barbs 172 converge into a sharp tip 174 that permits the tissue anchor 158 to penetrate soft tissue. Once the tissue anchor 158 is advanced into soft tissue, the barbs 172 inhibit withdrawal of the tissue anchor 158 in response to a pulling force applied the tissue anchor 158. Desirably, the tissue anchor 158 is also constructed from a shape-memory material to provide elasticity to the tissue anchors 158. Accordingly, tissue anchors 158 may assume the precurved shape of the distal ends 166 of the delivery tubes 156. Furthermore, the barbs 172 may be configured to expand outwardly when the tissue anchor 158 is deployed from the delivery tube 156 to enhance the tissue anchor's 158 resistance to removal, as illustrated in FIG. 25. The barbs 172 may be held in a restrained position within the delivery tube 156 prior to deployment, as shown in FIG. 24.

Desirably, a deployment device, such as a pushrod 176, is positioned within each delivery tube 156 proximal of the tissue anchor 158. Desirably, a handle, or hub 178 is coupled to each pushrod 176 such that the pushrods 176 are advanced within the delivery tubes 156 when a pushing force is applied to the hub 178. Accordingly, the hub 178 may be pushed to advance the push rods 176 which, in turn, push the tissue anchors 158 to deploy them from the delivery tubes 156. Because the pushrods 176 are interconnected with the hub 178, the deployment of the tissue anchors 158 occurs substantially simultaneously. However, in alternative arrangements, the tissue anchors 158 may be deployable independently of one another.

FIGS. 26a-26f illustrate the system 150 being utilized to remodel an aortic valve AV to treat aortic insufficiency. Aortic insufficiency or regurgitation is a heart valve disease in which the aortic valve weakens or balloons, preventing the valve leaflets from closing tightly. This typically leads to backward flow of blood from the aorta A into the left ventricle LV. Over time, this condition could result in heart failure. Although the system 150 is advantageously well suited for treatment of aortic insufficiency, it can be used in, or adapted for use in, other remodeling applications as well.

Similar to the system 50, the catheter 152 preferably is advanced through the patient's vasculature to a position downstream from the aortic valve AV, as shown in FIG. 26a. Once the catheter 152 is properly positioned, the delivery tubes 156 may be deployed from the guide catheter 154 by advancement of the hub 164. As the delivery tubes 156 are advanced from the guide catheter 154, they assume their pre-curved shape of the distal ends 166 and move toward the wall of the aorta A. Preferably, the delivery tubes 156 are advanced until they pass through the wall of the aorta A, as illustrated in FIG. 26b. However, in some arrangements, the tissue anchors 158 may be configured to reside within the wall of the aorta A and, thus, the delivery tubes 156 may not pass completely through the aorta A. Advantageously, with the system 150, the tissue anchors 158 are disposed at a distal-most end of the catheter 152. That is, preferably no portion of the catheter 152 extends beyond the general position of the tissue anchors 158. Accordingly, the tissue anchors 158 may be deployed in close proximity to the valve AV (or other obstructing object) in comparison to devices that deliver anchors proximal of the distal-most end of the device.

Once the delivery tubes 156 are positioned, the tissue anchors 158 may be deployed from the delivery tubes 156 by advancement of the hub 178, as illustrated in FIG. 26c. The pushrods 176 and delivery tubes 156 may be retracted by retraction of the hubs 164 and 178, leaving the tissue anchors 158 disposed within the tissue of the aorta A, as illustrated in FIG. 26d. As described above, the suture 160 interconnects the tissue anchors 158 and tension may be applied to one or both of the suture ends 160a, 160b to move the tissue anchors 150a toward one another and reduce the cross-sectional dimension of the aorta A to achieve the desired remodeling of the aortic valve AV. Preferably, the suture is tightened until the leaflets of the aortic valve AV coapt to inhibit or prevent regurgitation, as illustrated in FIG. 26e.

FIGS. 27-30 illustrate another preferred system 200, which is configured to deploy tissue anchors into soft tissue of a patient. The illustrated system 200 includes a catheter assembly 202. The catheter assembly 202 preferably includes a guide catheter 204, a delivery catheter 206, and a tissue anchor deployment member, such as a pushrod 208. The guide catheter 204, delivery catheter 206 and pushrod 208 are assembled coaxially and are movable relative to one another, in a manner similar to the systems described above.

A proximal end of the guide catheter 204 defines a handle, or hub 210. A distal end of the guide catheter 204 preferably is adapted to receive a guide wire 212 (FIG. 30) which may be used to assist in directing the catheter 202, as is described in greater detail below. Specifically, a distal end of the guide catheter 204 includes an enlarged portion 214 that defines a passage 216, which extends in a direction generally parallel to a longitudinal axis of the guide catheter 204 and to the main lumen of the guide catheter 217. The passage 216 is configured to receive the guide wire 212 so that the guide catheter 204 may be advanced or retracted along the guide wire 212. In the illustrated arrangement, the enlarged portion and the passage 216 extends along only a portion of the distal end of the guide catheter 204, such as about 4 to 5 cm in one arrangement to provide for a quick set-up. However, in other arrangements, the passage 216 may extend for other distances, may extend the entire length of the guide catheter 204 or may be divided into a plurality of intermittent passage sections extending along a portion or the entire length of the catheter 204.

The delivery catheter 206 defines a handle, or hub 220 at its proximal end. The hub 220 permits the delivery catheter 206 to be manipulated by a user of the system 200. A distal end of the delivery catheter 206 preferably defines a beveled tip 222, which facilitates piercing of soft tissue. Desirably, the distal end portion of the delivery catheter 206 is configured to have a pre-set curved shape, as illustrated in FIG. 30. For example, the entirety or at least the distal end portion of the delivery catheter 206 may be constructed from a super-elastic or shape-memory material that is manipulated into a desired curved shape. Accordingly, the guide catheter 204 may function to restrain the delivery catheter 206 in a generally linear configuration while the delivery catheter 206 is stowed within the guide catheter 204. However, when the distal end portion of the delivery catheter 206 is deployed from the guide catheter 204, the distal end portion of the delivery catheter 206 tends to move toward its pre-curved shape. With such an arrangement, the longitudinal axis of the guide catheter 204 may be generally parallel to a surface of the soft tissue 224 and, when deployed, the distal end portion of the delivery catheter 206 may curve to penetrate the tissue 224 in a direction generally perpendicular to the longitudinal axis of the guide catheter 204.

The push rod 208 preferably is a solid, cylindrical elongate member which resides within the lumen of the delivery catheter 206. The pushrod 208 is movable within the lumen of the delivery catheter 206 and is positioned proximal of the tissue anchors 226. The pushrod 208 is configured to permit a user of the system 200 to deploy the tissue anchors 226 from the catheter 202.

Preferably, a plurality of tissue anchors 226 are loaded within the delivery catheter 206 to be deployed individually by the pushrod 208. Desirably, the tissue anchors 226 are interconnected by a line, such as a suture 228. Specifically, the suture 228 passes through an eyelet 230 of each tissue anchor and, preferably, is secured to the distal most tissue anchor 226. The free end of the suture 228 extends through the delivery catheter 206 and exits a proximal end of the catheter assembly 202. Tension may be applied to the free end of the suture 228 to draw the tissue anchors 226 towards one another after they have been implanted into tissue 224 to remodel the tissue 224 as desired. Desirably, the distal tip 232 of the tissue anchors 226 include a pair of barbs 234 that inhibit withdrawal of the tissue anchors 226 from the soft tissue 224.

FIGS. 31-36 illustrate yet another preferred system 250 which is configured to deploy a plurality of tissue anchors into soft tissue of a patient. The system 250 includes a catheter assembly 252. The catheter assembly 252 preferably includes a guide catheter 254 and a delivery catheter 256. In the illustrated arrangement, the guide catheter 254 includes a guide passage 258, which is configured to receive a guide wire to permit the guide catheter 254 to be passed over the guide wire, as is described in greater detail below. Preferably, the guide passage 258 is similar to the passage 216 of the guide catheter 204, described above.

In addition, desirably, the catheter assembly 252 also includes an elastic member, or a linear coil purse string device 260, an extension rod 262, and an actuator rod 264. Desirably, the linear coil purse string device 260 may be housed within a distal end portion of the guide catheter 254 and is carried by the delivery catheter 256, which is movable within the guide catheter 254. In the illustrated arrangement, the linear coil purse string device 260 is carried outside of the lumen of the delivery catheter 256. The extension rod 262 and actuator rod 264 extend through the lumen of the delivery catheter 256 and interact with the device 260, as is described in greater detail below.

The linear coil purse string device 260 includes a helically wound wire 270, having a first end 270a and a second end 270b. The first and second ends 270a, 270b may comprise end caps which encapsulate the ends of the coiled wire 270 to inhibit the wire 270 from damaging tissue. The ends 270a, 270b may be secured together by a lock nut 271. Specifically, the ends 270a, 270b may be received within cavities 271a, 271b of the lock nut 271, as is described in greater detail below.

Preferably, the coiled wire 270 is constructed from a super-elastic or shape-memory material and is expandable from its relaxed state. However, other stretchable, or elastic, materials or structures may also be used. The wound length of the device 260 is configured according to the specific anatomical structure into which it is designated for implantation. In one arrangement, the wire diameter preferably is between about 0.002 and 0.015 inches. The inner diameter of the wound coil (or size of the mandrel on which it may be wound) preferably is between about 0.010 and 0.125 inches. However, other suitable dimensions may also be used.

Desirably, a plurality of tissue anchor stowage members, or capsules 272, are spaced along the coiled wire 270. In one arrangement, the capsules 272 are positioned about every centimeter along the device 260. The capsules 272 may be secured to the coiled wire 270 by any suitable mechanism or technique, such as swaging, welding or gluing, for example. Preferably, the capsules 272 are generally cylindrical in shape and reside within the interior space defined by the coiled wire 270. Each tissue anchor stowage capsule 272 preferably houses a tissue anchor 274. The tissue anchor 274 is initially in a stowed orientation within the capsule 272 and is configured to be deployed therefrom, as illustrated in FIG. 34. The tissue anchor 274 initially resides within a generally cylindrical passage 276 defined by the capsule 272. An exit hole 278 communicates with the passage 276 and opens to an outer surface of the capsule 272. Desirably, the exit hole 278 is configured to permit at least a portion of the tissue anchor 274 to be deployed from the capsule 272.

Preferably, the tissue anchor 274 is substantially similar to the tissue anchors described above, and includes a tissue penetrating tip 280 and, desirably, a pair of barbs 282. The barbs 282 inhibit the tissue anchor 274 from withdrawing from tissue once the tissue anchor 274 has been deployed.

The tissue anchor 274 also includes an enlarged head 284 opposite the tissue penetrating tip 280. Desirably, the head 284 is sized and/or shaped such that the head 284 may not pass through the exit hole 278 and, thus, the tissue anchor 274 remains secured to the capsule 272 even after deployment.

As described above, the actuator rod 264 extends through the delivery catheter 256 and through the device 260. A proximal end of the actuator rod 264 is accessible from external a proximal end of the guide catheter 254 and delivery catheter 256 so that the actuator rod 264 may be manipulated by a user of the system 250. Preferably, the actuator rod 264 passes through a space within the coiled wire of the device 260 and through the passages 276 of each tissue anchor stowage capsule 272.

The actuator rod 264 includes an enlarged actuation head 266, which is initially positioned distal of the distal most tissue anchor capsule 272. The actuator head 266 of the actuator rod 264 is configured such that, when the actuator rod 264 is retracted, the actuator head 266 contacts the head 284 of tissue anchor 274 and pushes the tip 280 of the tissue anchor 274 through the exit hole 278. Preferably, the head 284 of the tissue anchor 274 moves into the exit hole 278 (and out of the passage 276) a sufficient distance to permit the enlarged head 266 of the actuator rod 264 to pass through the passage 276 and exit the capsule 272. However, preferably, the tissue anchor 274 is not completely separated from the capsule 272. The actuator rod 264 may be continued to be retracted to deploy the tissue anchor 274 of each capsule 272 in a similar manner.

The extension rod 262 is configured to maintain the linear coil purse string device 260 in an expanded configuration relative to its relaxed configuration. That is, the extension rod 262 secures the device 260 in an extended orientation wherein it is longer than its relaxed orientation. The extension rod 262 passes through the delivery catheter 256 and through the device 260. A proximal end of the extension rod 262 is accessible external of the proximal end of the catheter assembly 252 so that the extension rod 262 can be manipulated by a user of the system 250.

The extension rod 262 extends through a passage 290 within each of the tissue anchor stowage capsules 272. Preferably, the passage 290 is generally parallel to the passage 276. Desirably, the extension rod 262 includes a plurality of steps in which the diameter of the extension rod 262 increases. Each step 292 contacts a proximal end surface of the capsule 272 to hold each tissue anchor stowage capsule 272 in a desired position relative to each other capsule 272. Thus, preferably, the extension rod 262 includes an equal number of steps 292 as capsules 272. Desirably, the spacing of the steps 292 determines the length of extension of the device 260. Preferably, the diameter of the extension rod 262 decreases in a direction from the proximal end toward the distal end such that the extension rod 262 may be retracted without interference between the steps 292 and the tissue anchor stowage capsules 272. Thus, once the extension rod 262 is retracted, the linear coil purse string device 260 is permitted to move from its extended orientation toward its relaxed orientation and remodel the tissue in which the device 260 is implanted.

Figure 37:
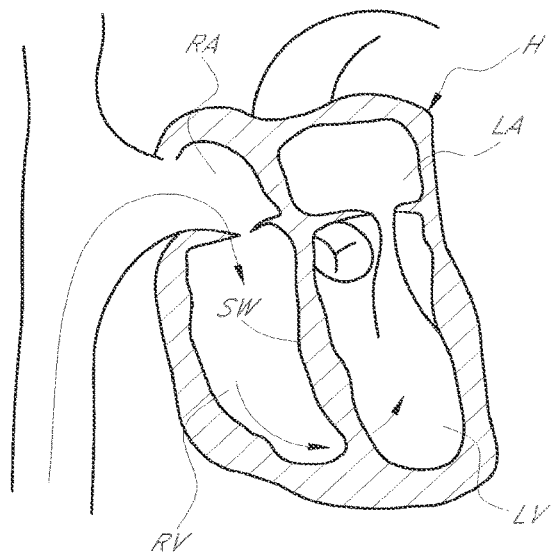
FIG. 37 is a vertical cross-sectional view of a patient's heart illustrating a preferred path of access to the left ventricle from the right ventricle and through the septal wall.
Figure 38:
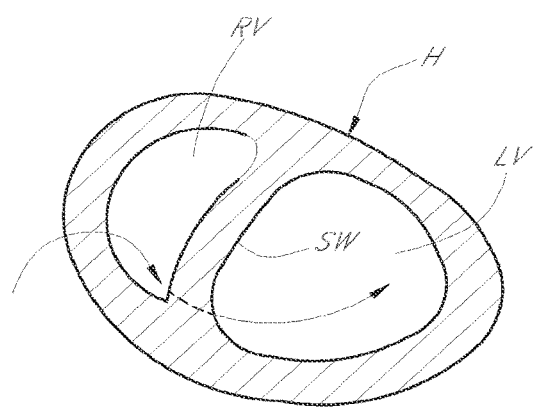
FIG. 38 is a horizontal cross-sectional view of the heart illustrating the preferred access path of FIG. 37.

The above described systems 200 and 250, as well as the system 50 of FIGS. 1-3, are particularly well suited for remodeling the left ventricle of a patient's heart. In one method of remodeling the left ventricle, access to the left ventricle is through a transeptal path. That is, access to the left ventricle is gained by creating an access passageway through the septal wall SW between the right ventricle RV and the left ventricle LV and passing the catheter from the right ventricle RV, through the septal wall SW, to the left ventricle LV. FIGS. 37 and 38 illustrate one preferred access pathway for gaining access to the left ventricle LV of a patient's heart H. Such an approach advantageously reduces or minimizes the potential complications of crossing the aortic valve in the case of a retrograde approach, or crossing the atrial septal and the mitral valve in the case of an antegrade approach.

Figure 39A:
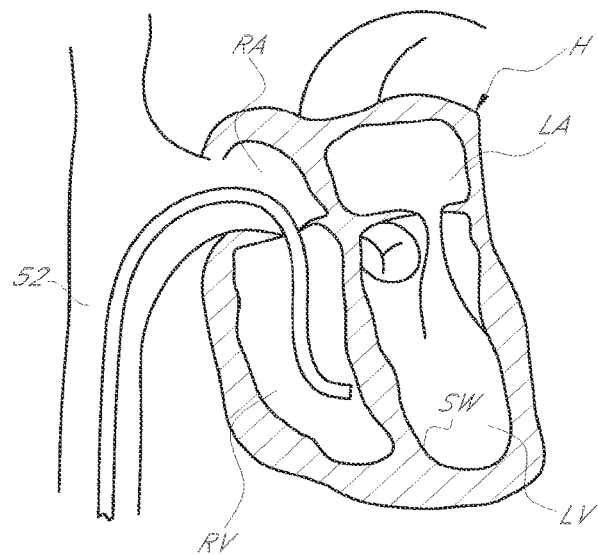
FIGS. 39a through 39h illustrate the catheter of FIG. 1 being used to deliver a purse string device, which includes a plurality of tissue anchors, to remodel the left ventricle of a patient's heart.
Figure 39B:
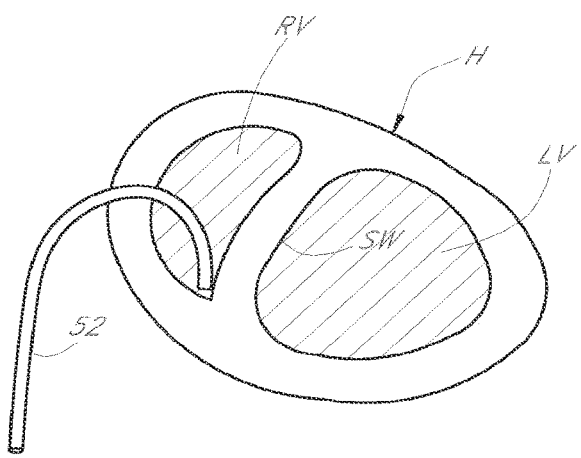
Figure 39C:
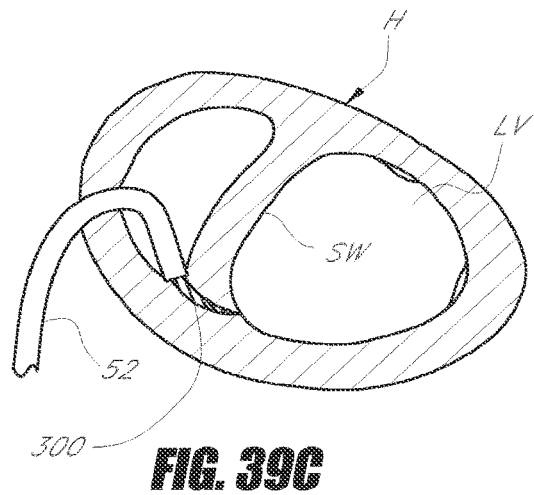
Figure 39F:
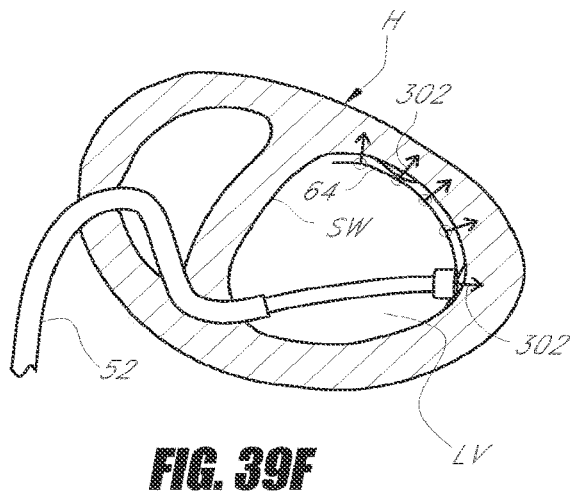
Figure 39D:
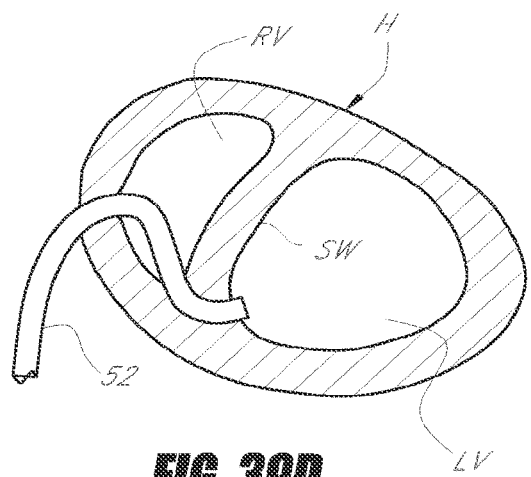

FIGS. 39a through 39h illustrate the system 50 of FIGS. 1-3 being utilized to remodel the left ventricle LV of a patient's heart H and reaching the left ventricle LV along an access path as shown in FIGS. 37 and 38. As illustrated in FIG. 39a, the catheter 52 is introduced through vasculature to the right ventricle. Once in place within the right ventricle RV, the distal end of the catheter 52 is abutted against the septal wall SW, preferably near a junction of the septal wall SW and the outer wall, or anterior wall portion, of the heart H (FIG. 39b). A transeptal device 300 is utilized to create an access pathway through the septal wall (FIG. 39c) and the catheter 52 is advanced through the passageway (FIG. 39d). Preferably, the transeptal device 300 is a conventional device known in the art for creating a transeptal passageway, such as a Mullins sheath, for example. However, other suitable devices or methods may also be used.

Figure 39G:
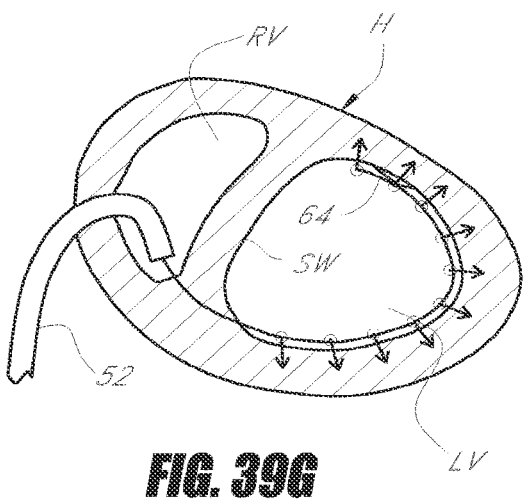
Figure 39E:
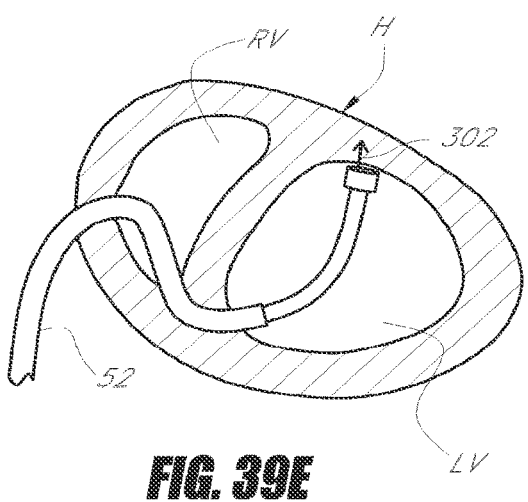
Figure 39H:
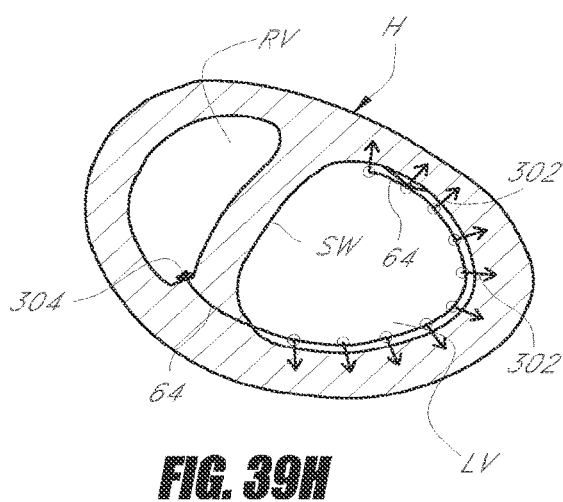

The catheter 52 is then advanced toward a desired tissue location within the left ventricle LV, such as a junction between the septal wall SW and the external wall of the heart H opposite the access pathway, as illustrated in FIG. 39e. Tissue anchors 302, which may be of any suitable construction, such as one of the various constructions described above, are introduced at desired spaced locations preferably in a semi-circular pattern within the external wall of the heart H (FIG. 39f). Desirably, when used in this method, one end of the suture 64 is secured to the first tissue anchor 302. Once the tissue anchors 302 have been positioned, preferably the free end of the suture 64 is passed through the access passageway within the septal wall SW and pulled tight to draw the tissue anchors 302 towards one another to remodel the left ventricle LV, as illustrated in FIG. 39g.

A retaining structure, such as a knot 304, can then be created in the suture 64 within the right ventricle RV to abut the septal wall SW to secure the tissue anchors 302 in the desired spacing to maintain the remodeling of the left ventricle LV. As described above, the knot 304 may be created outside of the patient and advanced through the catheter 53 by a suitable device, such as a knot pusher. Preferably, in some arrangements, a pledget (not shown) or similar member is positioned between the septal wall SW and the knot 304 to increase the surface area acting on the septal wall SW and inhibit the knot from being pulled through the septal wall SW. In addition, other alternative devices or methods for maintaining tension on the suture 64 may also be used. The illustrated method has the advantage of using the septal wall SW as a back stop for tying off the suture 64, which is a relatively simple method of maintaining tension on the suture 64.

Figure 40A:
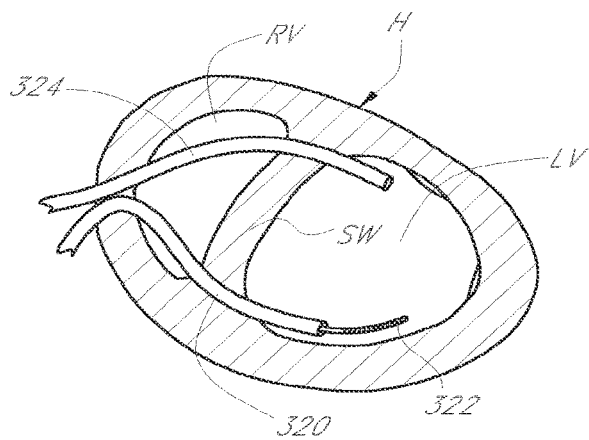
FIGS. 40a through 40h illustrate a preferred method of deployment of multiple tissue anchors interconnected by a line, such as a suture, within the left ventricle of a patient. Preferably, the tissue anchors and suture are deployed with the system of FIGS. 27-29.

FIGS. 40a-40j illustrate another preferred method for remodeling the left ventricle LV of a patient's heart H. In this illustrated method, preferably, the system 200 of FIGS. 27-30 is utilized. Initially, a first catheter 320 and a guide wire 322 are routed through vasculature to the right ventricle RV and through the septal wall SW to the left ventricle LV. A second catheter 324 is similarly advanced to the left ventricle LV, preferably to an opposite side of the left ventricle LV from the first catheter 320 and through a separate access passageway, as illustrated in FIG. 40a.

Figure 40D:
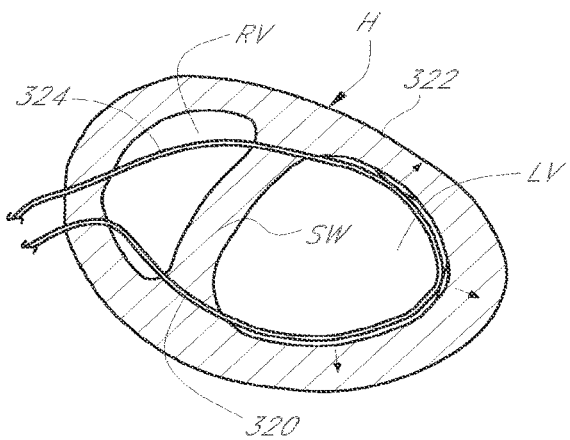
Figure 40B:
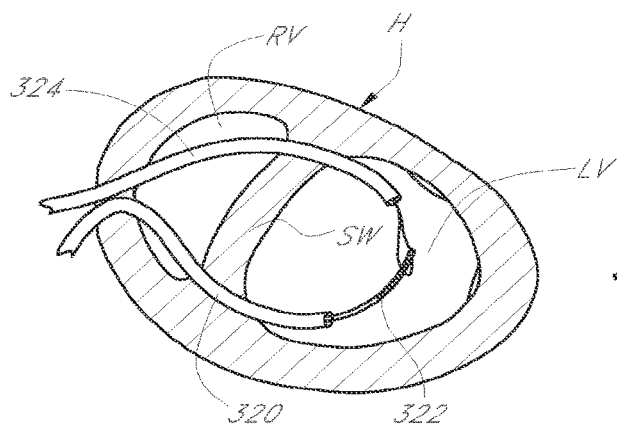
Figure 40E:
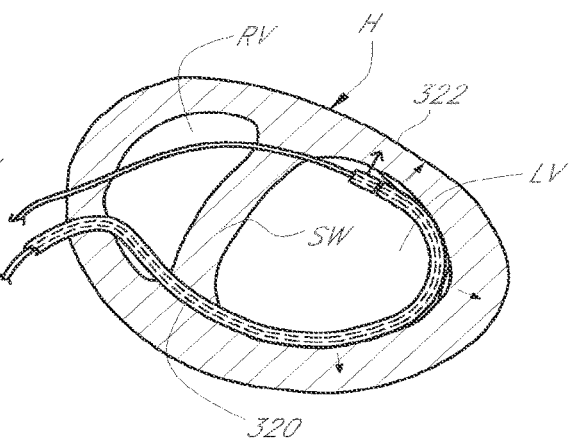
Figure 40C:
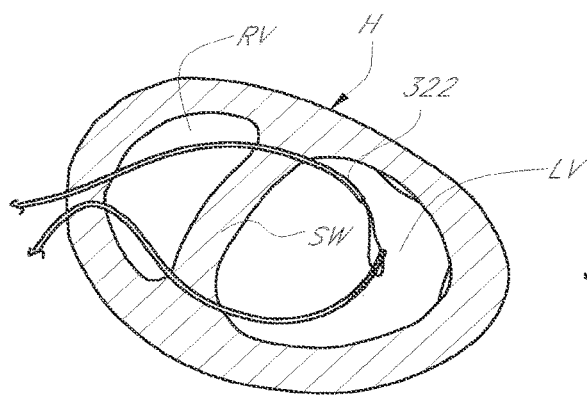
Figure 40F:
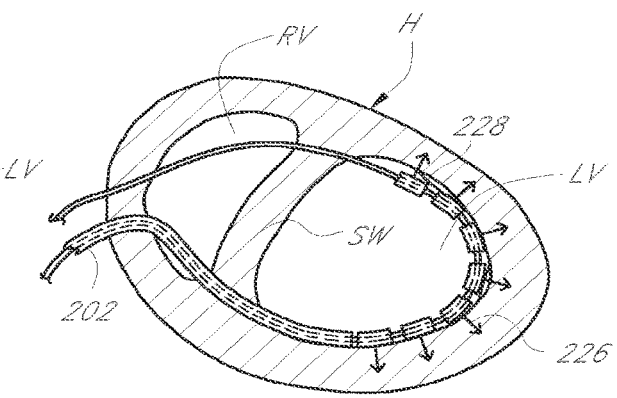

A retrieval device 326 is advanced through the second catheter 324 and is used to grasp the guide wire 322, as shown in FIG. 40b. The retrieval device 326 may be of any suitable construction to permit the retrieval of the guide wire 322, such as one of the devices disclosed in U.S. Pat. Nos. 5,522,819 or 5,868,754, for example, the entireties of which are incorporated by reference herein and made a part of this specification. The guide wire 322 can then be pulled through the second catheter 324 such that both ends of the guide wire 322 are located external of the patient. The catheters 320 and 324 may then be removed from the patient, leaving the guide wire 322 in place, as illustrated in FIG. 40c.

The user of the system 200 may apply a force to the free ends of the guide wire 322 to force the portion of the guide wire 322 within the left ventricle LV against the interior surface of the wall of the heart H, as shown in FIG. 40d. Accordingly, the guide wire 322 may be used to reduce the amount of motion due to the heart beat during deployment of the tissue anchors 226. Subsequent to the positioning of the guide wire 322, the catheter 202 may be advanced over the guide wire 322 until a distal end portion of the catheter 202 is within the left ventricle LV, as shown in FIG. 40e. Tissue anchors 226 may then be deployed within the external wall of the left ventricle LV as described above with reference to FIGS. 27-30 and shown in FIG. 40f.

Figure 40G:
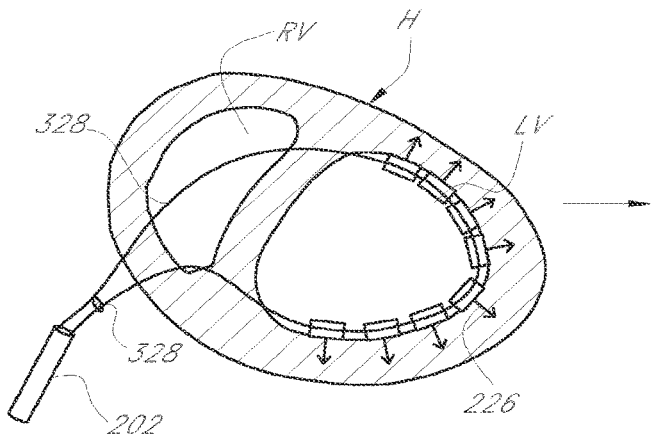
Figure 40H:
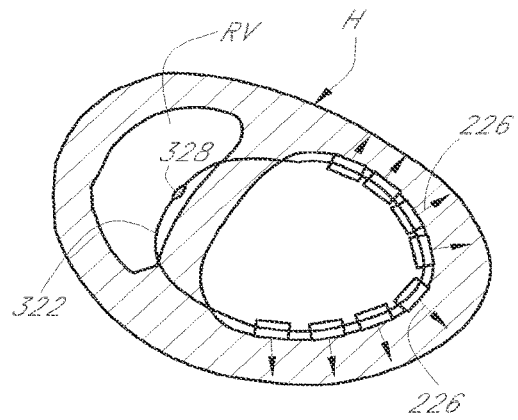

Once all the anchors had been placed, tension may be applied to the suture 228 interconnecting the tissue anchors 226 to draw the tissue anchors 226 towards one another and remodel the left ventricle. Preferably, a knot 328 may be created in the free ends of the suture 228 external of the patient and advanced through the catheter 202 to secure the free ends together and maintain tension on the suture 228, as illustrated in FIG. 40g. Preferably, the knot 328 is positioned within the right ventricle RV such that the portion of the suture 228 and knot 328 rest against the septal wall SW within the right ventricle RV to maintain the left ventricle LV in its remodeled orientation, as illustrated in FIG. 40h. This method may be used to reduce to the volume of the left ventricle LV to treat congestive heart failure or to reposition the papillary muscles to improve mitral valve function, among other therapeutic uses.

Figure 41A:
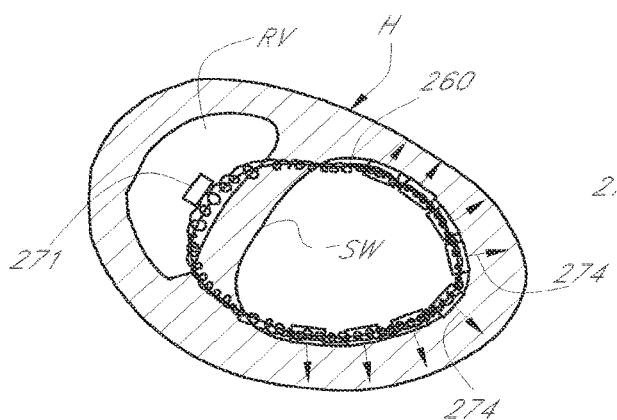
FIGS. 41a and 41b illustrate a preferred method of utilizing a linear coil purse string device to remodel the left ventricle of a heart.
Figure 41B:
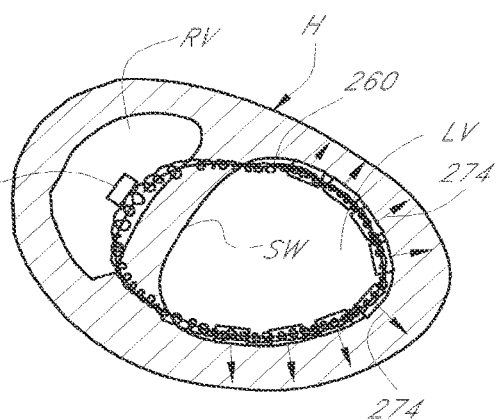

FIGS. 41a and 41b illustrate a similar method using the system 250 of FIGS. 31-36. In this method, once the linear coil purse string device 260 has been implanted within the left ventricle LV, the ends 270a and 270b are secured together within the right ventricle RV, such as by the lock nut 271 (as described above with reference to FIG. 33) or another suitable method. As described above, the tissue anchors 274 may be positioned within the heart H while the device 260 is in a stretched state. Desirably, the stretched state of the device 260 is no more than about 6 to 8 percent of the elastic limit of the material. Once the extension rod 262 is removed, the device 260 preferably retracts towards its relaxed state, thereby remodeling the left ventricle LV. The resistance to stretching of the device 260 assists in inhibiting excessive enlargement of the ventricle LV. This method may be used to reduce to the volume of the left ventricle LV to treat congestive heart failure or to reposition the papillary muscles to improve mitral valve function, among other therapeutic uses.

Figure 42A:
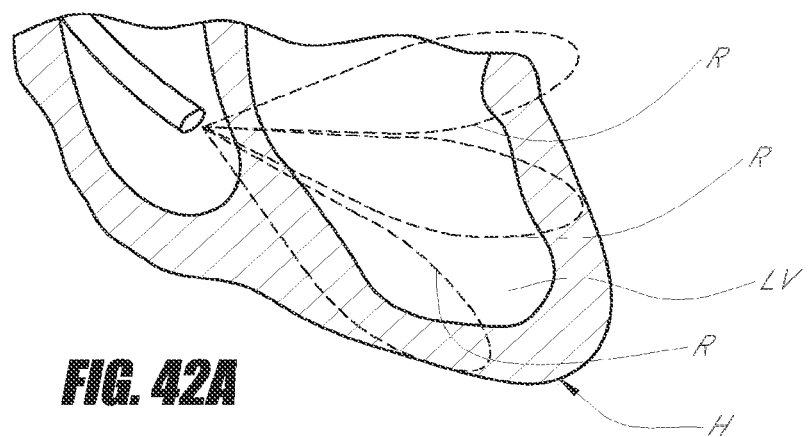
FIG. 42a illustrates another preferred arrangement of multiple purse strings within the left ventricle, wherein the purse string rows originate from a common point and are inclined relative to one another.
Figure 42B:
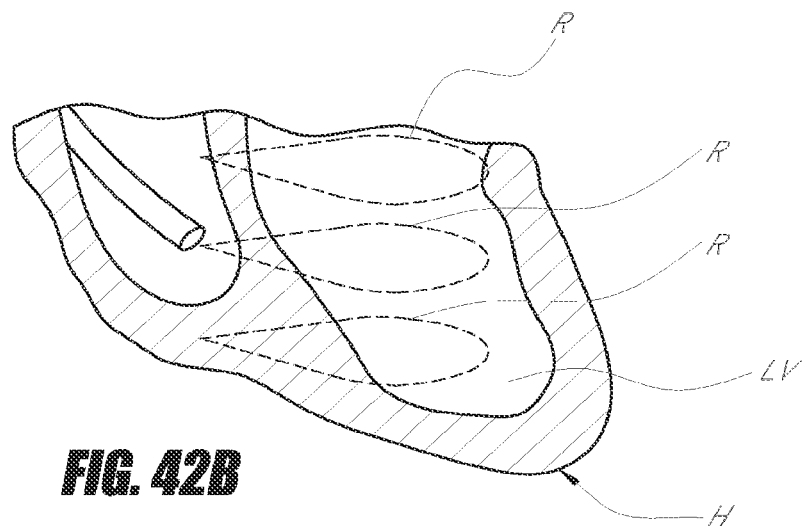
FIG. 42b illustrates a first arrangement of multiple purse strings within the left ventricle wherein the purse string rows are oriented generally parallel to one another.
Figure 43:
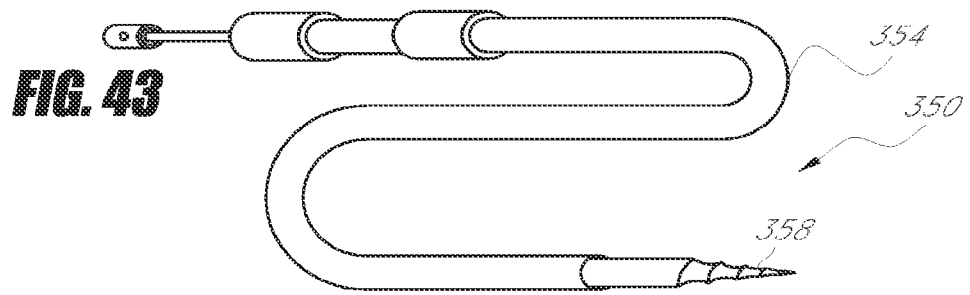
FIG. 43 is a perspective view of another tissue remodeling system including a catheter assembly having certain features, aspects and advantages of the present invention. The catheter assembly of FIG. 43 includes multiple co-axial components.
Figure 44:
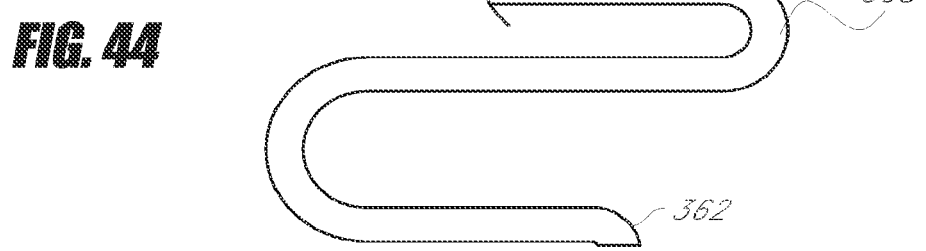
FIG. 44 illustrates a tissue tunneling member of the catheter assembly of FIG. 43.
Figure 45:
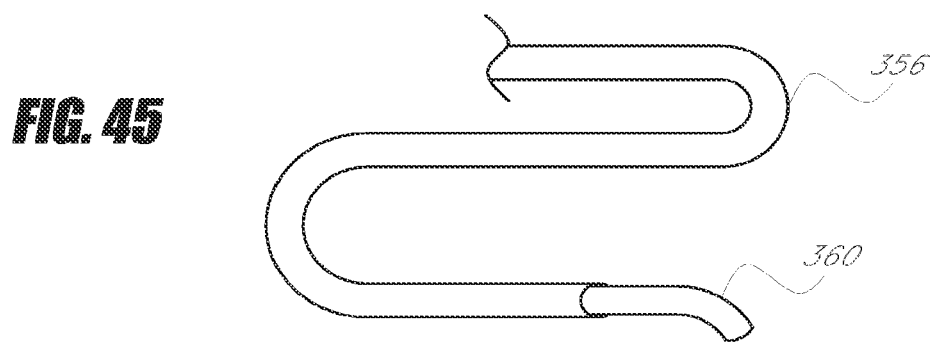
FIG. 45 illustrates a steering catheter of the catheter assembly of FIG. 43.
Figure 46:
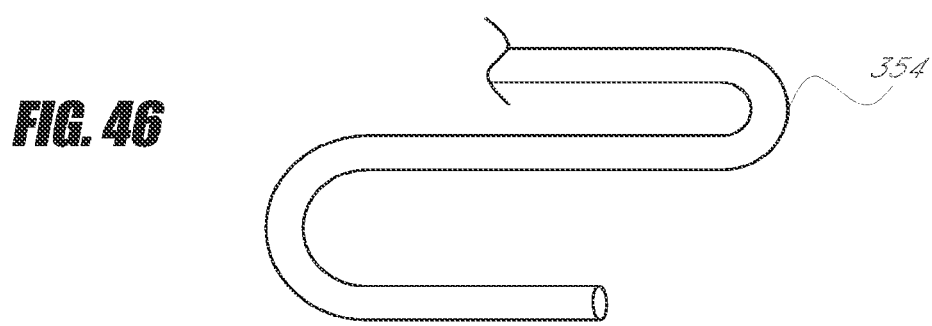
FIG. 46 illustrates a guide catheter of the catheter assembly of FIG. 43.

With reference to FIGS. 42a and 42b, as will be appreciated by one of skill in the art, multiple rows R of tissue anchors may be implanted within the left ventricle LV. For example, with reference to 42a, the multiple rows R may converge at a common point and be inclined relative to one another. Alternatively, the multiple rows R may be positioned substantially parallel to one another, depending on the desired shape of the remodeled ventricle. Other suitable relative orientations of the rows R of tissue anchors may also be used, including arrangements wherein two or more rows R intersect with one another.

FIGS. 43-46 illustrate yet another system 350 for remodeling soft tissue of a patient. Preferably, the system 350 includes a catheter assembly 352. The catheter assembly 352 preferably includes a guide catheter 354 and a delivery catheter 356. A tunneling device 358 is received within the delivery catheter 356.

Desirably, the delivery catheter 356 has a pre-curved distal end portion 360 that may be constrained in a generally linear configuration when positioned within the guide catheter 354. However, when deployed from the guide catheter 354, the distal end portion 360 of the delivery catheter 356 preferably tends to move toward its pre-curved configuration. As described above, the pre-curved shape of the delivery catheter 356 may be configured by heat setting or otherwise manipulating a super-elastic or shape-memory material. Furthermore, the distal end of the guide catheter 354 may be deflectable, such as in a manner similar to the guide catheters described previously.

The tunneling device 358, preferably is an elongate rod with a tissue penetrating tip 362. The tip 362, in one arrangement, may include one or more helical flutes such that when the tunneling device 358 is rotated, the tip 362 tends to facilitate passage through tissue. The tunneling device 358 preferably is constructed from a super-elastic or shape-memory material to provide a desired degree of flexibility. However, other suitable materials may also be used, such as stainless steel, for example.

The delivery catheter 356 and tunneling device 358 may be advanced and rotated relative to one another and the guide catheter 354 to permit the tunneling device 358 to move through tissue in a desired tunneling path. Preferably, the tunneling device 358 is configured to carry an end of a suture or other line, through the passage created by the tunneling device 358, as is described in greater detail below. However, in other arrangements, the tunneling device 358 may be configured to carry other suitable cinching devices, such as an elastic member similar to the coiled member 270, with or without the tissue anchor capsules 272.

Figure 47:
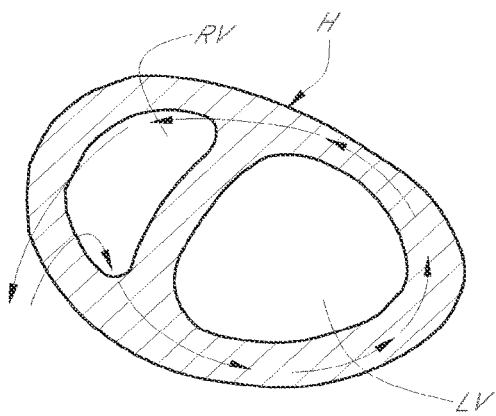
FIG. 47 illustrates a preferred path of deployment of the system of the catheter of FIG. 43.
Figure 48A:
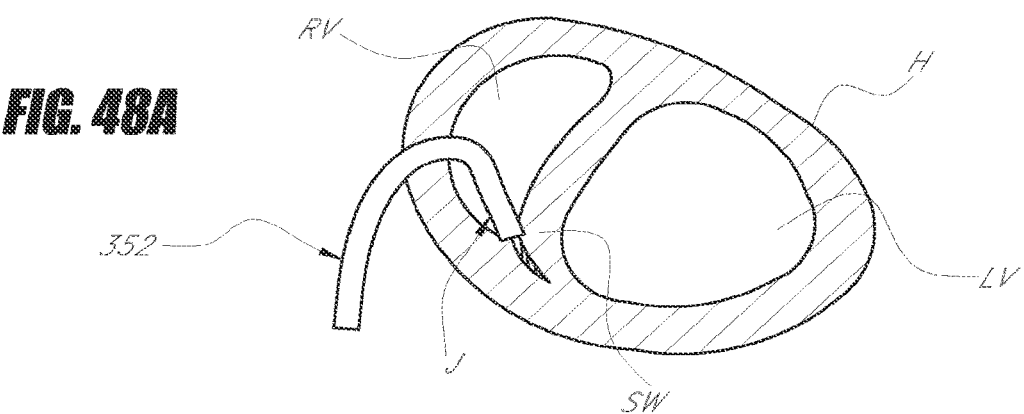
FIGS. 48a through 48h illustrate the system of FIG. 43 being utilized to place a suture within a passage through the myocardial wall surrounding the left ventricle of a patient's heart.

FIG. 47 illustrates one desired path for the tunneling device 358 to facilitate placement of a suture to remodel the left ventricle LV of a patient's heart H. In addition, FIGS. 48a through 48h illustrate a preferred method of utilizing the system 350 to pass a cinching member, such as suture 364, through the heart wall and around the left ventricle LV. With reference to FIG. 48a, preferably by methods similar to those described immediately above, access is gained to the right ventricle RV through the patient's vasculature. A catheter 362 preferably is utilized to gain access to the right ventricle RV and provide a path to permit the catheter assembly 352 to be advanced through the catheter 362 to the right ventricle RV. Once inside the right ventricle RV, the catheter assembly 352 is positioned at a junction J of the septal wall SW and the external wall of the heart H. The tunneling device 358 may be advanced from the guide catheter 354 by a pushing force and, preferably, simultaneous rotation so that the tip 362 bores into the tissue.

Figure 48B:
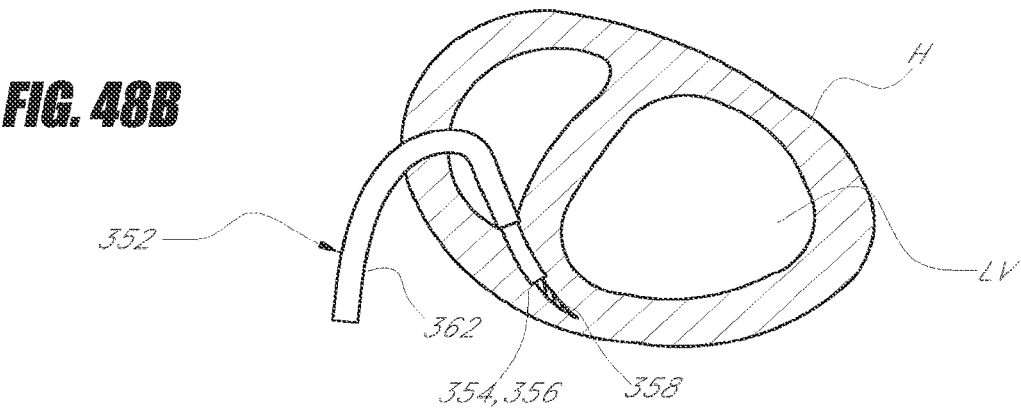
Figure 48C:
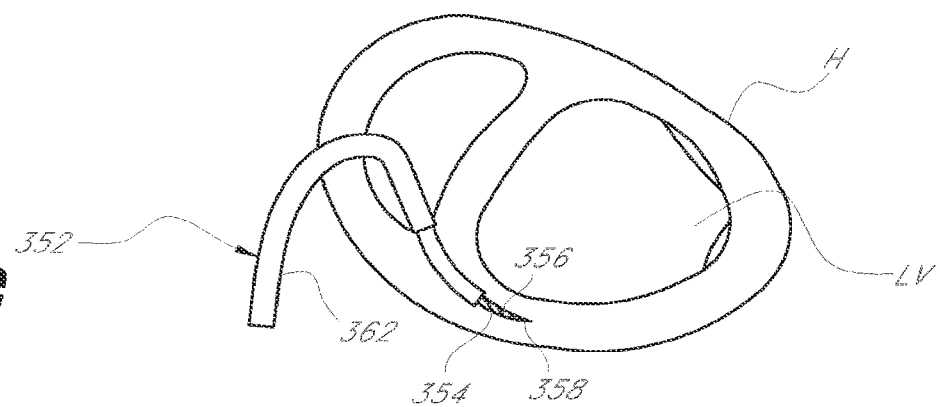
Figure 48D:
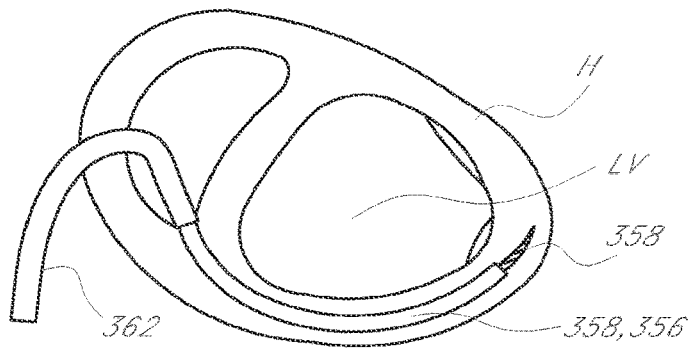
Figure 48E:
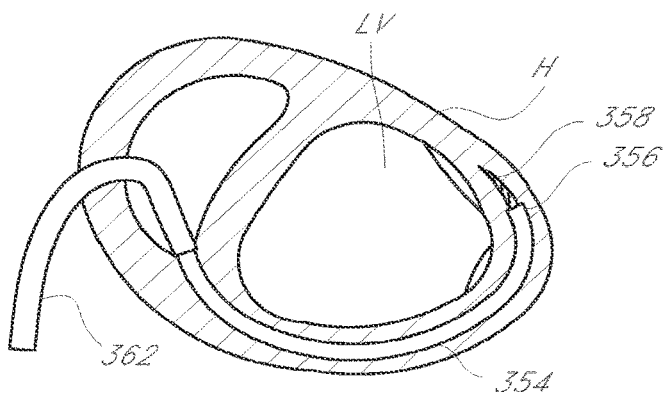
Figure 48F:
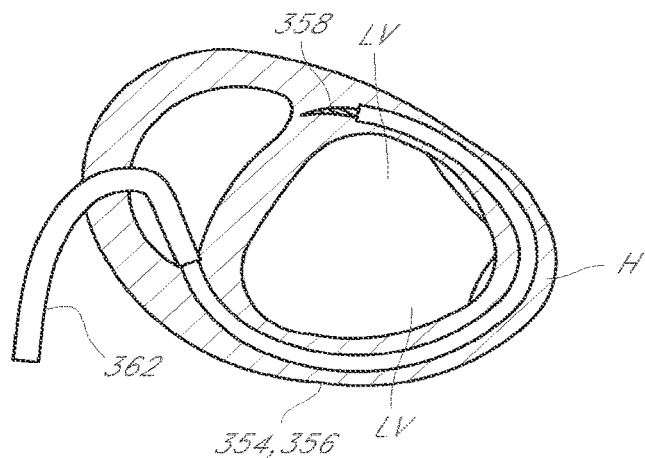
Figure 48G:
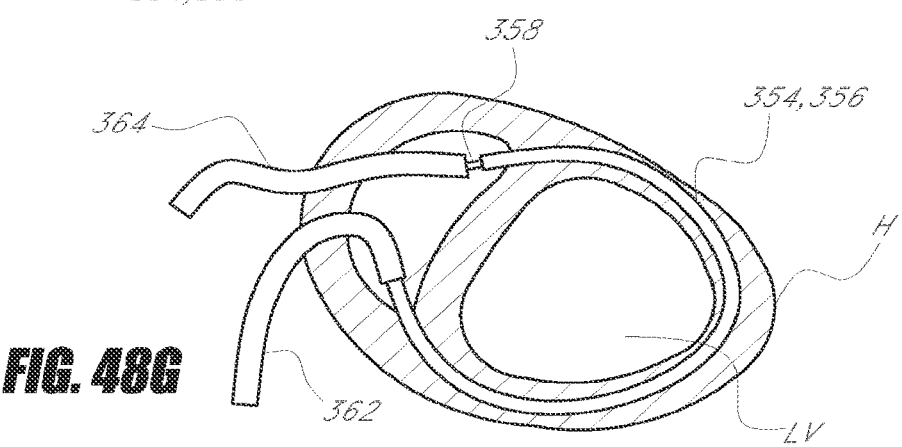

With reference to FIG. 48b, the guide catheter 354 and the delivery catheter 356 may be advanced along the tunneling device 358 after the tunneling device 358 has created a path through the heart wall. The delivery catheter 356 may be advanced from the guide catheter 354 such that the distal end portion 360 of the delivery catheter 356 assumes a desired pre-curved configuration. Accordingly, the delivery catheter 356 may be used as a steering device to urge the tunneling device 358 in a desired direction. The extent that the delivery catheter 356 is exposed from the guide catheter 354, along with the rotational position of the delivery catheter 356 relative to the guide catheter 354, may be selected and modified throughout the procedure to achieve a desired tunneling path of the tunneling device 358. In this manner, as illustrated successively in FIGS. 48c through 48g, the tunneling device 358 may be steered in a path through the external wall of the heart H circumscribing the left ventricle LV until the tunneling device 358 reenters the right ventricle RV, preferably at a junction between the septal wall SW and external wall of the heart H opposite its entry point. A retrieval tube, or retrieval catheter 364, may be introduced to the right ventricle RV by a suitable method to receive the tip of the tunneling device 358 so that the device 358 may be advanced through the catheter 362 until it may be retrieved from the proximal end of the retrieval catheter 364.

Figure 48H:
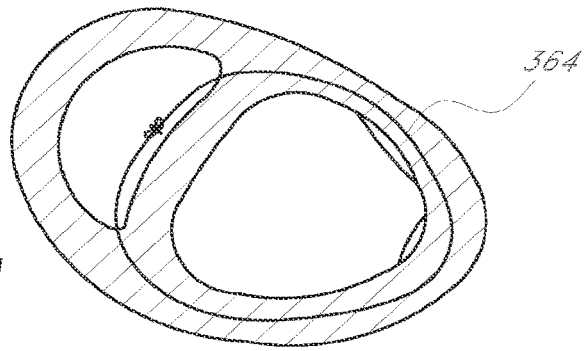

Accordingly, such a method permits the tunneling device 358 to not only create a tunnel, or passage, through the heart wall, but to also pass a cinching device, such as the suture 364, through the passage. The suture 364, or other cinching device, may then be pulled, or cinched, to remodel the left ventricle LV. Preferably, as illustrated in FIG. 48h, the suture 364 is tied off into a knot to maintain the remodeled orientation in a manner similar to that described above. Pledgets may be used if desired to spread the load acting on the heart wall from the knot to a larger area. The system 350 and described method may be used to remodel the left ventricle LV, such as reducing the volume to treat congestive heart failure or repositioning the papillary muscles to improve mitral valve function. In addition, the system 350 and method may be used to remodel other body cavities as well.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. For example, the present systems may be utilized for tissue attachment, tissue compression, tissue cinching, tissue tying, tissue remodeling, tissue apposition and holding tissue in a desired position. Furthermore, while the present tissue remodeling systems and methods have been described in the context of particularly preferred embodiments, the skilled artisan will appreciate, in view of the present disclosure, that certain advantages, features and aspects of the system may be realized in a variety of other applications, many of which have been noted above. Additionally, it is contemplated that various aspects and features of the invention described can be practiced separately, combined together, or substituted for one another, and that a variety of combination and sub-combinations of the features and aspects can be made and still fall within the scope of the invention. Thus, it is intended that the scope of the present invention herein disclosed should not be limited by the particular disclosed embodiments described above, but should be determined only by a fair reading of the claims.

What is claimed is:

1. A device for remodeling a heart valve, comprising:
a flexible outer body having a generally tubular shape, the outer body being configured to be placed into an implanted curved configuration about a heart valve; and
a plurality of tissue anchors located within the flexible outer body and being configured to be individually and consecutively anchored into heart tissue, wherein when the tissue anchors are anchored into heart tissue the tissue anchors extend extending from within the outer body to outside of the outer body and distal ends of the tissue anchors being configured to extend into heart tissue; and
wherein each tissue anchor is moveable relative to adjacent tissue anchors to remodel heart tissue.

2. The device of claim 1, wherein the flexible body has a deployment longitudinal length and an implanted longitudinal length that is shorter than the deployment longitudinal length, and the flexible body is moveable from the deployment longitudinal length to shorter implanted longitudinal length.

3. The device of claim 2, wherein moving the outer body from the deployment longitudinal length to the shorter implanted longitudinal length moves the tissue anchors relative to adjacent tissue anchors to remodel heart tissue.

4. The device of claim 1, wherein the flexible outer body comprises a coiled member.

5. The device of claim 4, wherein the coiled member comprises a coiled wire.

6. The device of claim 1, wherein the tissue anchors include a head at a proximal end thereof and a tissue penetrating tip at the distal end thereof.

7. The device of claim 6, wherein the head of the tissue anchor has a circular cross-section.

8. The device of claim 6, wherein the tissue anchor includes a rod between the head of the tissue anchor and the tissue penetrating tip, wherein a cross-section of the head is larger than a cross-section of the rod.

9. A device for remodeling a heart tissue, comprising:
a guide catheter sized and configured to be moved through a patient's vasculature to the desired remodeling site in the heart;
a delivery catheter receivable within the guide catheter and movable relative to the guide catheter;
a heart remodeling implant being configured to be delivered through the delivery catheter, the heart remodeling implant comprising:
a flexible outer body having a generally tubular shape, the outer body being configured to be placed into an implanted curved configuration about heart tissue, the outer body having a first deployment longitudinal length and second implanted longitudinal length, wherein the second implanted longitudinal length is shorter than the first deployment longitudinal length;
a plurality of tissue anchors that are configured to be individually and consecutively anchored into heart tissue;
wherein when the heart remodeling implant is implanted, distal ends of the tissue anchors extend through the outer body, said distal ends of the tissue anchors being configured to anchor to heart tissue; and
wherein moving the outer body from the first deployment longitudinal length to the second implanted longitudinal length cinches the tissue anchors relative to adjacent tissue anchors to remodel heart tissue.

10. The device of claim 9, wherein the flexible outer body comprises a coiled member.

11. The device of claim 10, wherein the coiled member comprises a coiled wire.

12. The device of claim 9, wherein each tissue anchor includes a head at a proximal end thereof and a tissue penetrating tip at the distal end thereof.

13. The device of claim 12, wherein the head of the tissue anchor has a circular cross-section.

14. The device of claim 12, wherein the tissue anchor includes a rod between the head of the tissue anchor and the tissue penetrating tip, wherein a cross-section of the head is larger than a cross-section of the rod.

15. The device of claim 9, further including an anchor deployment member removably positionable within the outer body, the anchor deployment member configured to move tissue anchors into an implanted position.

16. The device of claim 15, wherein the anchors are configured to be consecutively moved into the implanted position.

* * * * *